United States Patent
Kim et al.

(10) Patent No.: US 9,855,320 B2
(45) Date of Patent: Jan. 2, 2018

(54) ANGIOGENIN FOR TREATMENT OF GLAUCOMA

(75) Inventors: Jae Chan Kim, Seoul (KR); Doo Hwan Oh, Seoul (KR); Kwang Sic Joo, Seoul (KR); Yeoun Sook Chun, Seoul (KR); Sung Wook Wee, Seoul (KR); Kyoung Woo Kim, Seoul (KR)

(73) Assignee: CHUNG-ANG UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 53 days.

(21) Appl. No.: 14/348,051

(22) PCT Filed: Feb. 27, 2012

(86) PCT No.: PCT/KR2012/001466
§ 371 (c)(1),
(2), (4) Date: Jul. 27, 2014

(87) PCT Pub. No.: WO2013/051767
PCT Pub. Date: Apr. 11, 2013

(65) Prior Publication Data
US 2014/0370087 A1 Dec. 18, 2014

(30) Foreign Application Priority Data

Oct. 6, 2011 (KR) .................. 10-2011-0101899
Oct. 7, 2011 (KR) .................. 10-2011-0102598

(51) Int. Cl.
*A61K 38/46* (2006.01)
*C07K 14/515* (2006.01)
*A61K 45/06* (2006.01)
*G01N 33/68* (2006.01)
*A61K 38/18* (2006.01)

(52) U.S. Cl.
CPC ............ *A61K 38/465* (2013.01); *A61K 45/06* (2013.01); *C07K 14/515* (2013.01); *G01N 33/6863* (2013.01); *A61K 38/1891* (2013.01); *G01N 2333/52* (2013.01); *G01N 2500/10* (2013.01)

(58) Field of Classification Search
None
See application file for complete search history.

(56) References Cited

U.S. PATENT DOCUMENTS

| 5,714,463 A * | 2/1998 | York ............... A61K 33/24 514/16.5 |
| 2002/0010320 A1* | 1/2002 | Fett ............... C07K 16/22 530/387.3 |
| 2011/0123995 A1 | 5/2011 | Greenway et al. |
| 2011/0151016 A1 | 6/2011 | Mcdonagh et al. |
| 2012/0165292 A2 | 6/2012 | Zeldis |

FOREIGN PATENT DOCUMENTS

| KR | 10-0923173 B1 | 10/2009 | | |
| KR | 10-2011-0036536 A | 4/2011 | | |
| WO | WO 98/40487 | * 9/1998 | ............ C12N 15/12 |
| WO | WO 99/58126 | * 11/1999 | ............ A61K 31/37 |
| WO | WO2005/101982 | * 11/2005 | | |
| WO | WO2009/043455 | * 4/2009 | ............ A61K 38/18 |

OTHER PUBLICATIONS

Translation of Chen from the Journal of Nachang University, 2010; 50: 7-11; 19 pages total.*
Machine translation of CN 101422603, downloaded on Feb. 13, 2017 from http://www.google.com/patents/CN101422603A?cl=en; 5 pages total.*
Wu et al., Ann Neurol. 2007; 62: 609-617.*
Tokuriki and Tawflik, Current Opinion in Structural Biology 2009, 19: 596-604.*
Chen abstract; the English abstract from Nanchang Daxue Xuebao, Yixueban, 2010; 50: 7-11; 1 page total.*
Saxena et al., JBC 1992; 267: 21982-21986.*
Stitt, Br J Ophthalmol. 2001; 85:746-753.*
Chopra et al., Ophthalmology 2008;115:227-232.*

* cited by examiner

*Primary Examiner* — Christina M Borgeest
(74) *Attorney, Agent, or Firm* — Revolution IP, PLLC

(57) ABSTRACT

The present invention provides a pharmaceutical composition for the prevention or treatment of glaucoma, wherein the pharmaceutical composition includes angiogenin or a fragment thereof as an active ingredient. Angiogenin or a fragment thereof according to the present invention activates aqueous humor outflow due to NO generation increase, Schlemm's canal expansion, and intercellular interval widening, thereby reducing intraocular pressure. Accordingly, angiogenin and a fragment may be useful for the prevention and treatment of glaucoma.

2 Claims, 14 Drawing Sheets

ANGIOGENIN FOR TREATMENT OF GLAUCOMA

CROSS REFERENCE TO PRIOR APPLICATIONS

This application is the 35 U.S.C. §371 National Stage of International application PCT/KR2012/001466 filed on Feb. 27, 2012; which claims priority to Korean applications 10-2011-0101899 and 10-2011-0102598 filed on Oct. 6, 2011 and Oct. 7, 2011, respectively. The entire contents of each of the above-identified applications are hereby incorporated by reference.

TECHNICAL FIELD

The present invention relates to a novel use for the prevention and treatment of glaucoma based on intraocular pressure reduction effects of angiogenin. In particular, the present invention relates to a novel use of angiogenin for the prevention and treatment of inflammatory disease.

PRIOR ART

Angiogenin induces angiogenesis in a yangyo film of a chicken embryo, and also induces angiogenesis in cornea and meniscus of knee joints of rabbits. Angiogenin acts as follows: angiogenin activates a protease for decomposing basal membrane and extracellular matrix, promotes adhesion and infiltration of vascular endothelial cell, and forms canaliculus of vascular cell, thereby promotes angiogenesis. Other known angiogenesis promoting materials are VEGF, bFGF, IL-12 and so on, and these materials are being studied for the treatment of ischemic diseases developed in the heart and peripheral circulates.

Angiogenin is a protein having 14.4 kDa of a long single chain consisting of 123 amino acids, and induces cell proliferation and angiogenesis with the help of other angiogenesis factors. In particular, it is known that the nuclear translocation process of angiogenin is a critical phase in the process of angiogenesis. However, still, how angiogenin acts in vivo is not clear. A recent study shows that the concentration of angiogenin is increased in tears collected from closed eyes during at night. This study explained body defense mechanism according to the increase in the concentration of various growth factors, such as angiogenin.

Although there are many controversies over change in intraocular pressure between day and night, many studies report that night-time intraocular pressure is higher than day-time intraocular pressure, and accordingly, glaucoma patients may experience optic nerve injury due to the increase in night-time intraocular pressure. On the other hand, some recent studies show that night-time intraocular pressure is rather lower than day-time intraocular pressure, and this result may be due to the decrease in production of aqueous humor and the increase in aqueous humor outflow.

Etiology of glaucoma has not been clearly revealed. However, the increase in intraocular pressure is known as a major risk factor of glaucoma. A cause for the increased intraocular pressure is known to be increased resistance of Schlemm's canal and trabecular meshwork in the route of aqueous humor outflow due to several pathological change. Also, some studies reported that in addition to mechanical injury to optic nerves due to high intraocular pressure, vascular factors are engaged in the development of glaucoma. That is, when hemoperfusion of optic nerve is decreased by unknown reasons, optic disk of optic nerve may be ischemically injured. Also, there are several efforts to identify etiology of glaucoma in terms of immunology. According to an ischemic theory, glaucoma may be understood as a chronic neurodegenerative disease caused by continuous loss of optic nerve axon and retinal ganglion cell, which is explained as topical ischemia due to vasocontriction. That is, since vasocontriction is a characteristic sign of immunity-related disease, glaucoma can also be understood as an immune response. This assumption is supported by the fact that autoimmune disease patients are more likely to have glaucoma. Also, even when a normal intraocular pressure range is maintained, optic nerve of normal intraocular pressure glaucoma patients is continuously injured. This shows that glaucoma develops due to, in addition to intraocular pressure, ischemic change, immunological reasons, and so on.

Many medicaments have been developed based on these etiology of glaucoma, and from among these medicaments, prostaglandin-based medicaments are often used as a therapeutic agent for glaucoma since they induce change in extracellular matrix of ciliary muscle to increase aqueous humor outflow through an uveoscleraloutflow channel, thereby effectively reducing intraocular pressure. Some studies imply the likelihood that the major mechanism of prostaglandin (PG) preparations is mediated by the generation and modulation of nitric oxide (NO) that induces muscular relaxation, and other studies report intraocular pressure reduction effects directly obtained from NO.

The change in intraocular pressure between day-time and night-time and the change in the angiogenin concentration in tears may be associated with body defense mechanism against intraocular pressure. Based on this assumption, the inventors of the present invention studied change in aqueous humor outflow channel due to angiogenin, and the resulting change in intraocular pressure, and found that angiogenin interacts with a material that produces NO and an immune mediation material, thereby showing intraocular pressure reduction effects.

Immunity protects tissues and cells of the body from the outside, and excessive immune response, such as autoimmune response, causes major tissue necrosis and apoptosis, damaging major tissues and organs, and more seriously, causing death. Autoimmune disease, infective disease and so on are treated by appropriately suppressing and inducing excessive immune response. In particular, An eyeball tissue is known for an easily afflicted autoimmune disease, such as uveitis. Optic diseases related to etiology, such as cataract, glaucoma, or age-related macular degeneration, are explained based on immunological mechanism.

In particular, most glaucoma, which is one of major causes of blindness, is a normal intraocular pressure glaucoma in the Asia region including South Korea, and other factors than intraocular pressure are suggested as a cause for glaucoma. For example, an immunological factor may cause glaucoma. Also, in the case of keratitis or stevens-Johnson syndrome, chemical burn, and so on, eyeballs structurally change due to various internal or external factors derived from ocular tissue damage, and ocular immune response made by immune cells and immune mediating material causes corneal neoangiogenesis and opacity, thereby causing decreased visual acuity. These immunological ocular diseases may be suppressed and treated by modulating secondary immune inflammatory responses through immunological avoidance.

Angiogenin has not sufficiently been studied in the ocular field, and like a vascular endothelial growth factor (VEGF), is a secretory protein inducing angiogenesis. Angiogenin is ribonuclease (RNase), and in particular, is well known as to induce growth of tumor cell and angiogenesis. Some recent studies report that as for amyotrophic lateral sclerosis (ALS), angiogenin gene mutation is associated with the development of ALS, and when administered, angiogenin shows neuroprotection effects on neurodegenerative disease, such as ALS and Parkinson's disease. Due to these study results, research into angiogenin is being actively performed. Nadine et al. disclosed that angiogenin is expressed in trophoblastic cell collected from human placenta, trophoblast basement membrane, endothelial basal lamina, fetal blood vessel, fetal and maternal red blood cells, amnion cell and so on, and argued that their finding shows angiogenin is engaged in, in addition to angiogenesis, homeostasis maintenance in blood vessels and tissues, and maternal immune tolerance with respect to fetus.

However, studies for identifying immunological actions of angiogenin in inflammatory disease have not been conducted, and in particular, effects of angiogenin on corneal opacity, neoangiogenesis in chronic ocular inflammations have not been studied at all. So, the inventors of the present invention studied whether in the ocular field, angiogenin acts as a major factor in modulating immunity in various immune disease, such as glaucoma that is neurological disease and develops due to immune etiology, and found excellent effects of angiogenin related thereto, thereby completing the present invention.

DETAILED DESCRIPTION OF THE INVENTION

Technical Field

The present invention provides a novel use of angiogenin for the prevention and treatment of glaucoma.

The present invention also provides a novel use of angiogenin for the prevention and treatment of inflammatory ocular disease.

Technical Solution

The present invention provides a pharmaceutical composition for the prevention or treatment of glaucoma, wherein the pharmaceutical composition includes angiogenin or a fragment thereof as an active ingredient.

The present invention also provides an ophthalmic agent for the prevention or treatment of glaucoma, wherein the ophthalmic agent includes angiogenin or a fragment thereof as an active ingredient and additionally, an ophthalmically acceptable carrier.

In an embodiment of the present invention, the fragment of angiogenin may be a polypeptide having an amino acid sequence set forth in SEQ ID NO: 1.

The present invention also provides a pharmaceutical composition for the prevention or treatment of inflammatory disease, wherein the pharmaceutical composition includes angiogenin as an active ingredient.

Advantageous Effects

Angiogenin or a fragment thereof according to the present invention activates aqueous humor outflow due to NO generation increase, Schlemm's canal expansion, and intercellular interval widening, thereby reducing intraocular pressure. Accordingly, angiogenin and a fragment may be useful for the prevention and treatment of glaucoma.

Also, angiogenin according to the present invention suppresses corneal neoangiogenesis during initial inflammatory response, protects ganglion cells, and reduces the amount of IL-1a, TGF-β, SDF-1 and caspase-3 at inflammatory sites. Accordingly, angiogenin may be useful for the prevention and treatment of inflammatory disease, in detail, chronic ocular inflammation or a normal intraocular pressure glaucoma that is associated with immunological mechanism.

BRIEF DESCRIPTION OF THE DRAWINGS

FIG. 16 shows images of anterior ocular segment, FIG. 17 shows a graph showing grade evaluation results obtained therefrom, and FIG. 18 shows a graph showing corneal new vessel—area measurements.

FIG. 19 shows an image showing test results of reverse transcription polymerase chain reaction, FIG. 20 is a graph of results obtained on the third day after injuring, and FIG. 21 is a graph of results obtained on the seventh day after injuring.

BEST MODE

Figure 1:
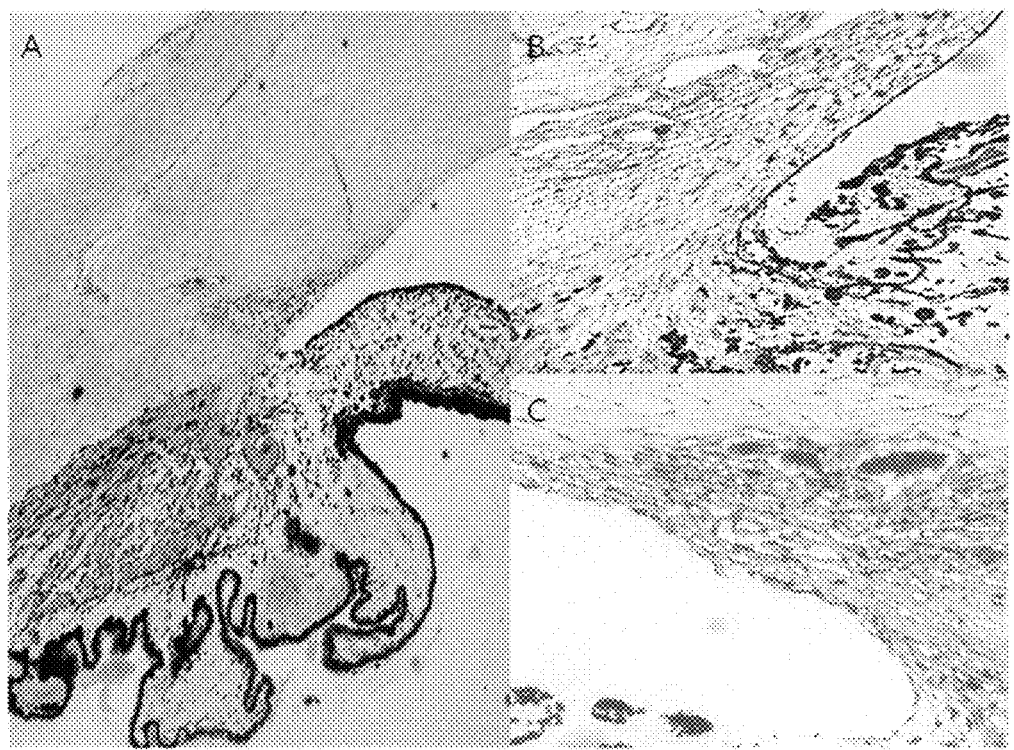
FIG. 1 shows images showing immunohistochemical staining results with respect to cadaveric ocular anterior chamber angle. A shows an image of Haematoxylin-Eosin staining, B shows an image of IHC staining on angiogenin, and C shows an image of IHC staining on IDO.

The present invention provides a pharmaceutical composition for the prevention or treatment of glaucoma, wherein the pharmaceutical composition includes angiogenin or a fragment thereof as an active ingredient.

As confirmed in embodiments of the present invention, angiogenin or a fragment thereof according to the present invention induces, when applied to glaucoma rat model, schlemm's canal expanding and intercellular interval widening, thereby significantly reducing intraocular pressure. In addition, in NO measurement tests, instilling of angiogenin caused a significant increase in NO concentration inside glaucoma rat model aqueous humor. Accordingly, it is confirmed that angiogenin according to the present invention, like commercially available prostaglandin preparations, induces intraocular pressure reduction even with intraocular pressure reduction mechanism achieved by muscular relaxation caused by NO generation increase. Also, the same effects are obtained when only a C-terminal fragment of angiogenin is used.

Accordingly, the composition including angiogenin or a fragment thereof according to the present invention may be used as an active ingredient in the prevention and treatment of glaucoma.

Accordingly, the present invention provides a pharmaceutical composition for the prevention or treatment of glaucoma including angiogenin or a fragment thereof as an active ingredient, a use of angiogenin or a fragment thereof for the preparation of a therapeutic agent for glaucoma, and a method of treating glaucoma including administrating a therapeutically effective amount of angiogenin or a fragment thereof to a subject.

In an embodiment of the present invention, the fragment of angiogenin indicates a domain of an entire amino acid sequence of angiogenin, and is not limited thereto as long as the domain has the same effects as those obtainable from angiogenin. For example, the fragment of angiogenin may be a C-terminus, a 15 to 20 amino acid sequence of a C-terminus, or a polypeptide having an amino acid sequence set forth in SEQ ID NO: 1.

In other embodiments, since the angiogenin or a fragment thereof activates aqueous humor outflow by NO generation increase, Schlemm's canal expanding, and intercellular interval widening, thereby reducing intraocular pressure, angiogenin or a fragment thereof may be useful for the prevention and treatment of glaucoma.

In an embodiment of the present invention, a pharmaceutical composition for the prevention or treatment of glaucoma including angiogenin or a fragment thereof as an active ingredient may further include at least one appropriate additive selected from a carrier, an excipient, a disintegrating agent, a sweetener, a coating agent, a bulking agent, a polishing agent, a lubricant, an aromatic agent, an antioxidant, a buffer, a bacteriostatic agent, a diluent, a dispersant, a surfactant, a binder, and a lubricant, which are all conventionally used in preparing a pharmaceutical composition.

In detail, a carrier, an excipient, and a diluent may be selected from lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. Examples of a solid preparation for oral administration are a tablet, a pill, a powder, a granule, and a capsule, and such a solid preparation may be prepared by mixing the composition with at least one excipient, for example, starch, calcium carbonate, sucrose, lactose or gelatin. In addition to the simple excipient, lubricants, such as magnesium stearate and talc, may also be used herein. A liquid preparation for oral administration may be a suspension, a liquid for internal use, an emulsion, or a syrup, and includes various excipients, such as a wetting agent, a sweetening agent, an aromatic agent, and a preservative, in addition to simple diluents such as water and liquid paraffin widely used in the art. A preparation for non-oral administration includes a sterile aqueous solution, a non-aqueous solvent, a suspension, an emulsion, a lyophilized preparation, or a suppository. A vegetable oil such as propylene glycol, polyethylene glycol, or olive oil, or an injectable ester such as ethyloleate may be used as the non-aqueous solvent or suspension. A base of the suppository that may be used herein may include witepsol, macrogol, Tween 61, cacao butter, laurin butter or glycerogelatin.

In other embodiments, the pharmaceutical composition for the prevention or treatment of glaucoma including angiogenin or a fragment thereof as an active ingredient may be formulated into a granule, a powder, a coated tablet, a tablet, a pill, a capsule, a suppository, a gel, a syrup, a liquid extract, a suspension, an oil, a dripping agent, or a liquid, by using a conventional method.

In an embodiment of the present invention, the pharmaceutical composition may be administered to a subject by using a conventional method. For example, the composition may be administered to a subject intravenously, arterially, subcutaneously, intramuscularly, inter-arterially, interperitoneally, intranasally, inhalation, topically, rectally, orally, ophthalmically, or intradermally.

In detail, the pharmaceutical composition for the prevention or treatment of glaucoma including angiogenin or a fragment thereof as an active ingredient is an ophthalmically acceptable composition, and may be formulated into a dripping agent and administered intra-ophthalmically.

Accordingly, the present invention provides an ophthalmic agent for the prevention or treatment of glaucoma including angiogenin or a fragment thereof as an active ingredient and an ophthalmically acceptable carrier.

The "ophthalmically acceptable carrier" has a wide range of meaning, and herein, includes any material or composition that includes and is capable of releasing angiogenin or a fragment thereof. Conventionally, the ophthalmically acceptable carrier may be water or aqueous solution, or a suspension. In some embodiments, the ophthalmically acceptable carrier may also be the same oil as used in the preparation of an ointment and a polymer matrix, which are used for an ocular additive.

The ocular composition may additionally include at least one selected from the group consisting of a surfactant, an adjuvant containing an additional medicament, a buffer, an anti-oxidant, a stress adjuster, a preservative, a thickener, and a viscosity reformer. Additives for use in formulations may include sodium chloride, EDTA, benzalkonium chloride, sorbic acid, methylparaben, propylparaben, chlorohexidine, glycerine, and sodium perborate.

A desirable dose of the angiogenin or fragment thereof may vary according to the conditions and weight of a subject, the kind and stage of a disease, the type of a drug, and the route and period of administration, but may be properly selected by those skilled in the art. According to an embodiment of the present invention, although not limited herein, a daily dose may be in a range of 0.01 to 200 mg/kg, or 0.1 to 200 mg/kg, or 0.1 to 100 mg/kg. The daily dose may be administrated once a day, or may be divided into several portions, which are then separately administered daily. However, the present invention is not limited thereto.

According to the present invention, the term "subject" may be a mammal including a human, but is not limited thereto.

The present invention also provides a method of screening for a glaucoma treatment drug, the method including administering a candidate drug to an animal model;

measuring a protein level of angiogenin in a biological sample of the animal model; and comparing the protein level with a protein level of a normal animal.

In an embodiment of the present invention, the candidate drug may be formed as a conventional formulation. For example, the candidate drug may be a liquid formulation for direct injection, a capsule formulation for oral administration, or an ophthalmic agent, but is not limited thereto.

The administration may be performed according to a conventional administration method. For example, the administration may be performed by direct injection, oral administration, or vascular injection. However, other methods may also be used for the administration.

The animal model may be Zebrafish, a mouse, a house rat, a guinea pig, a rabbit, a cat, a dog, sheep, a pig, cattle, a monkey, a baboon, or a chimpanzee.

In other embodiments, the biological sample is not limited, and may be a tissue, cell, blood, or plasma. For example, the biological sample may be a tear.

Measuring of the protein level may be performed by western blotting, ELISA, radioimmunoassay, radial immunodiffusion, Ouchterlony immunodiffusion, rocket immunoelectrophoresis, tissue immunostaining, immunoprecipitation assay, complement fixation assay, precipitin reactions, gel diffusion precipitin reaction, or a competitive or non-competitive known assay, such as agglutination assay, fluorescent immunoassay, protein A immunoassay, FACS, or protein chip. However, other methods may also be used to perform the measuring.

The ELISA includes, for example, a direct sandwich ELISA using a composite of an antibody and an antigen attached on a solid support and another marked antibody that recognizes the antigen, and an indirect sandwich ELISA in which a composite of an antibody and an antigen attached on a solid support is reacted with another antibody that recognizes the antigen, and then, a secondary marked antibody that recognizes the latter antibody is used.

If the protein level of angiogenin obtained by the measuring is higher than a protein level of angiogenin in normal animal due to the treatment with candidate drug, this means that the candidate drug can be used as a glaucoma treatment agent.

Also, the present invention provides a pharmaceutical composition for the prevention or treatment of inflammatory disease including angiogenin as an active ingredient.

As confirmed in the following Examples, the present invention newly discloses that angiogenin, which is conventionally known to involve in neoangiogenesis, rather suppresses corneal neoangiogenesis during initial inflammation, and also protects ganglion cells and reduces amounts of IL-1a, TGF-β, SDF-1 and caspase-3 at inflammatory site. Accordingly, the present invention provides a use of angiogenin of the prevention and treatment of inflammatory disease.

Thus, a pharmaceutical composition for the prevention or treatment of inflammatory disease, including angiogenin as an active ingredient, may be used for the treatment of inflammatory disease Accordingly, the present invention provides a pharmaceutical composition for the prevention or treatment of inflammatory disease including angiogenin as an active ingredient, a use of angiogenin for the preparation of an inflammatory disease treatment agent, and a method of treating inflammatory disease including administrating a therapeutically effective amount of angiogenin to a subject.

In an embodiment of the present invention, the inflammatory disease used herein refers to all disease including inflammation as a major lesion, and detailed examples of the inflammatory disease are septicemia, arteriosclerosis, bacteremia, a systemic inflammatory response syndrome, a multiple organ dysfunction syndrome, cancer, osteoporosis, paradentitis, systemic lupus erythematosus, rheumatoid arthritis, osteoarthritis, juvenile chronic arthritis, spondyloarthropathy, systemic scleroma, an idiopathic inflammatory disorder of muscle, Sjögren's syndrome, systemic vasculitis, sarcoidosis, autoimmune hemolytic anemia, autoimmune thrombocytopenia, thyroiditis, diabetes mellitus, an immune-mediated renal disease, a demyelinating disease in the central nervous system or peripheral nervous system, idiopathic demyelinating polyneuropathy, Guillain-Barre syndrome, chronic inflammatory demyelinating polyneuropathy, a hepatobiliary disease, infectious or autoimmune chronic active hepatitis, primary biliary cirrhosis, granulomatous hepatitis, sclerosing cholangitis, inflammatory bowel disease (IBD), ulcerative colitis, Crohn's disease, irritable bowel syndrome, gluten-irritable bowel disease, Whipple's disease, an autoimmune or immune-mediated skin disease, a bullous skin disease, erythema multiforme, contact dermatitis, psoriasis, an allergic disease, asthma, allergic rhinitis, atopic dermatitis, food sensitivity, urticaria, a pulmonary immune disease, eosinophilic pneumonia, idiopathic pulmonary fibrosis, hypersensitivity pneumonitis, a transplant rejection, and a graft-versus-host disease. In detail, the inflammatory disease may be chronic ocular inflammation.

As confirmed in the following Examples, regarding the corneal chemical burn model, a test group treated with angiogenin showed a significant decrease in corneal opacity and corneal neoangiogenesis, and amounts of IL-1a, TGF-β, SDF-1 and caspase-3 were also low. These results show that angiogenin prevents fibrosis during wound treatment, and also prevents neoangiogenesis and corneal deposits of many materials leaked from blood vessel to prevent corneal opacity. Accordingly, angiogenin may be useful for the treatment of chronic ocular inflammation.

In other embodiments, the inflammatory disease may be a normal intraocular pressure glaucoma associated with immunological mechanism.

As confirmed in the following Examples, regarding a chronic glaucoma model prepared by electrically ablating rat espisderal vein, an average intraocular pressure of a test group treated with angiogenin was significantly lower than that of a control, and a retinal density of the test group was not decrease. Accordingly, it is considered that angiogenin may act as a chemotactic factor to promote gathering of monocytes in aqueous humor outflow channel inside retina in blood vessel, and activated macrophage prevents apoptosis of retinal ganglion cell and increases the flow of aqueous humor outflow channel. Accordingly, due to intraocular pressure reduction effects and ganglion cell protection effects of angiogenin, angiogenin may be useful for use as a drug for the treatment of normal intraocular pressure glaucoma associated with immunological mechanism.

In an embodiment of the present invention, a pharmaceutical composition for the prevention or treatment of inflammatory disease including angiogenin as an active ingredient may further include at least one appropriate additive selected from a carrier, an excipient, a disintegrating agent, a sweetener, a coating agent, a bulking agent, a polishing agent, a lubricant, an aromatic agent, an anti-oxidant, a buffer, a bacteriostatic agent, a diluent, a dispersant, a surfactant, a binder, and a lubricant, which are all conventionally used in preparing a pharmaceutical composition.

In detail, a carrier, an excipient, and a diluent may be selected from lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil. Examples of a solid preparation for oral administration are a tablet, a pill, a powder, a granule or a capsule, and such a solid preparation may be prepared by mixing the composition with at least one excipient, for example, starch, calcium carbonate, sucrose, lactose or gelatin. In addition to the simple excipient, lubricants, such as magnesium stearate and talc, may also be used herein. A liquid preparation for oral administration may be a suspension, a liquid for internal use, an emulsion, or a syrup, and includes various excipients, such as a wetting agent, a sweetening agent, an aromatic and a preservative in addition to simple diluents such as water and liquid paraffin widely used in the art. A preparation for non-oral administration includes a sterile aqueous solution, a non-aqueous solvent, a suspension, an emulsion, a lyophilized preparation, or a suppository. A vegetable oil such as propylene glycol, polyethylene glycol, or olive oil, or an injectable ester such as ethyloleate may be used as the non-aqueous solvent or suspension. A base of the suppository that may be used herein may include witepsol, macrogol, Tween 61, cacao butter, laurin butter or glycerogelatin.

In other embodiments, the pharmaceutical composition for the prevention or treatment of inflammatory disease including angiogenin as an active ingredient may be formulated into a granule, powder, a coated tablet, a tablet, a pill, a capsule, a suppository, a gel, a syrup, a liquid extract, a suspension, an oil, a dripping agent, or a liquid, by using a conventional method.

In an embodiment of the present invention, the pharmaceutical composition may be administered to a subject by using a conventional method. For example, the composition may be administered to a subject intravenously, arterially, subcutaneously, intramuscularly, inter-arterially, interperitoneally, intranasally, inhalation, topically, rectally, orally, ophthalmically, or intradermally.

A desirable dose of the angiogenin may vary according to the conditions and weight of a subject, the kind and stage of a disease, the type of a drug, and the route and period of administration, but may be properly selected by those skilled in the art. According to an embodiment of the present invention, although not limited herein, a daily dose may be in a range of 0.01 to 200 mg/kg, or 0.1 to 200 mg/kg, or 0.1 to 100 mg/kg. The daily dose may be administrated once a day, or may be divided into several portions, which are then separately administered daily. However, the present invention is not limited thereto.

According to the present invention, the term "subject" may be a mammal including a human, but is not limited thereto.

Hereinafter, examples of the present invention will be described to help understanding of the present invention. However, these examples are provided herein for illustrative purpose only, and do not limit the scope of the present invention. Examples of the present invention are provided to fully explain the present invention to those skilled in the art.

<Example 1> Immunohistochemical Staining of Cadaveric Ocular Anterior Chamber Angle Eyeballs donated for research purposes were pre-fixed in a 4% paraformaldehyde solution for 6 hours, and then, a tissue thereof was cut to be perpendicular to cornea, including cornea, limbus, and conjunctival, and the obtained tissue was fixed at room temperature for 6 hours. The fixed tissue was rapidly frozen and then a frozen tissue section was prepared and attached to slide glass. Thereafter, for immunohistochemical staining, the tissue section was washed with distilled water for 10 minutes and then, treated with 1% hydrogen peroxide solution for 20 minutes and then, washed three times with 0.02M phosphate buffer solution and treated with normal horse serum for 30 minutes. Then, primary antibody of angiogenin and Indoleamine 2,3-dioxygenase (IDO) were applied thereto for 48 hours, and then the result tissue were washed with PBS, and then, secondary antibody was applied thereto at room temperature for 1 hour. When immunohistochemical staining was completed, the tissue was sealed by poly-mount and identified by optical microscopy.

The results are shown in FIG. 1. FIG. 1A shows a Haematoxylin-Eosin staining image, FIG. 1B shows an IHC staining image of angiogenin, and FIG. 1C shows an IHC staining image of IDO.

Referring to FIG. 1, when cadaveric ocular anterior chamber angle was subjected to angiogenin immunohistochemical staining, angiogenin was widely stained in anterior chamber angle from ciliary body to trabecular meshwork, and in particular, angiogenin was strongly expressed in from trabecular meshwork cell to Schlemm's canal and collecting duct near the trabecular meshwork cell (see FIG. 1B). Anterior chamber angle IDO staining results showed, like angiogenin staining results, strong IDO expression near trabecular meshwork cell (see FIG. 1C).

Ryu et al. discloses that IDO is expressed in body corneal and acts as a topical immune inhibitor to control corneal immunity. In light of this result and the disclosure, it is assumed that due to the IDO expression increase by angiogenin, topical immunity control is performed inside anterior chamber angle, and by doing so, the development of disease due to immunological etiology of glaucoma is suppressed.

<Example 2> Identification of Intraocular Pressure Change Due to Angiogenin Instillation in Glaucoma Rat Model (1) Preparation of Test Glaucoma Model Male white rats were used to prepare an episcleral venous ablation glaucoma model. The rat was anesthetized and a limbus periphery was divided into four portions, each of which was then subjected to 2 mm dissection at an interval of 90 degrees, and then, two radial conjunctival excisions were performed on upper dissection periphery. Tissue was pushed backward to make extra ocular muscle to be exposed and then, two back-side episcleral veins near superior rectus muscle and one ear-side episcleral vein near lateral rectus muscle were separated. Episcleral vein is distinguishable because it is located deeper than extra ocular muscle, has relatively low fluidity and a relatively large diameter, contains darker blood in vessel, and is connected to peripheral venous plexus. After surgical isolation of vein, the vein was lifted up by using 3 mm-width wooden spatula to be spaced apart from the peripheral tissue, and then, was subjected to electric ablation while being careful for the peripheral tissue not to have any thermal injury or any mechanical injury due to the contact. After the operation, a chloramphenical ophthalmic agent was administered thereto. Intraocular pressure was consecutively measured three or more times by using Tonopen (Solan, Fla., USA), and only reliable intraocular pressure values within 5% or less were recorded. Only used were rats that had higher intraocular pressure than that before the operation by 5 mmHg or more when measured on the first day, the third day, one week and two weeks before and after operation.

Also, steroid-induced glaucoma model was prepared as follows: 1% prednisolone was instilled twice a day in an amount of 4 μl for 30 days, and only rats that had higher intraocular pressure by 5 mmHg or more before operation were used.

Figure 2:
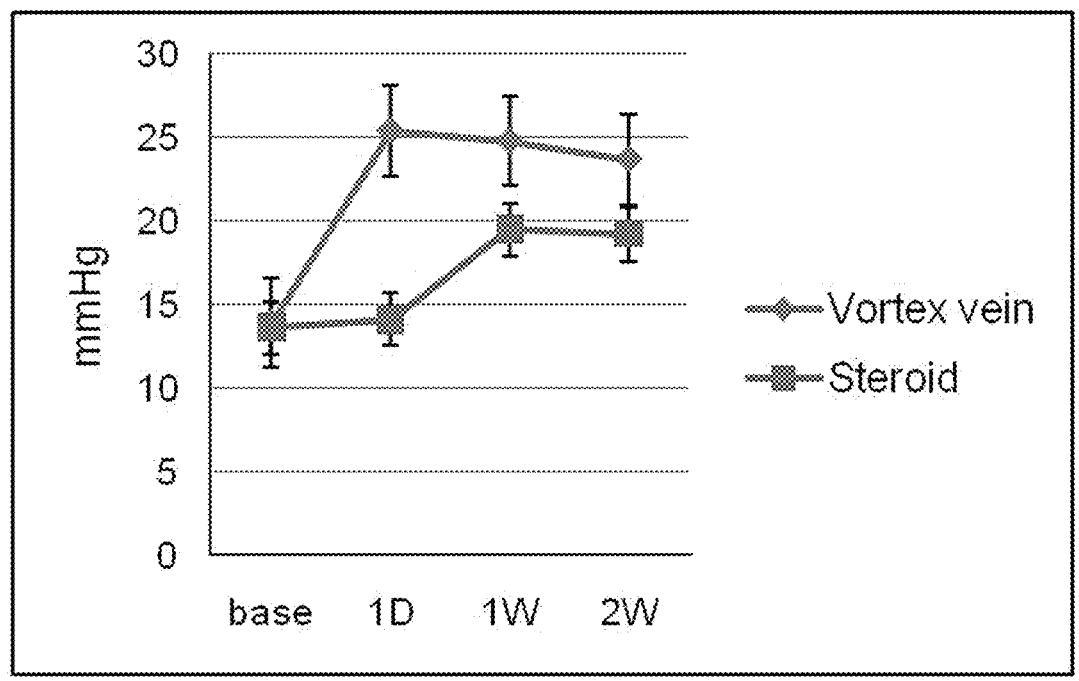
FIG. 2 is a graph showing intraocular pressure measurements on test glaucoma model.

The results are shown in FIG. 2.

Referring to FIG. 2, all rats subjected to episcleral venous ablation showed intraocular pressure increase, and in the case of the steroid-induced model, all rates excluding one death rat showed significant intraocular pressure increase. Glaucoma model was prepared by episcleral venous ablation, and when observed in 2 weeks, intraocular pressure before operation was 13.9±3.9 mmHg, and from the next day of the operation, intraocular pressure began to increase up to 25.4±3.5 mmHg, and until 2 weeks after the operation, intraocular pressure was maintained at 23.7±3.8 mmHg, that is, a significant intraocular pressure increase was maintained. The steroid-induced glaucoma model did not show significant intraocular pressure until one day after instillation. However, from one week, the intraocular pressure was increased to 19.5±2.2 mmHg, a significant increase compared to the value measured before instillation, that is, 13.6 mmHg, and up to 2 weeks, an intraocular pressure increase was confirmed.

(2) Identification of Intraocular Pressure Change Due to Angiogenin Instillation White rats were grouped as a physiological saline solution instillation group, an angiogenin (recombinant human angiogenin, R&D systems, USA) 50 μg/ml instillation group, an angiogenin fragment (angiogenin 108-122, SEQ ID NO: 1, BACHEM, USA) instillation group, and a latanoprost 50 μg/ml instillation group, and each group consisted of 6 rats, that is, 12 eyes. Instillation test was repeatedly performed on normal rats and glaucoma model rats. Ophthalmic agent was administered at 8 AM and 8 PM in an amount of 4 μl to compare day-time effects and night-time effects, and 1, 3, 6, 9, 12, and 24 hours after the instillation, intraocular pressure was measured.

Figure 3:
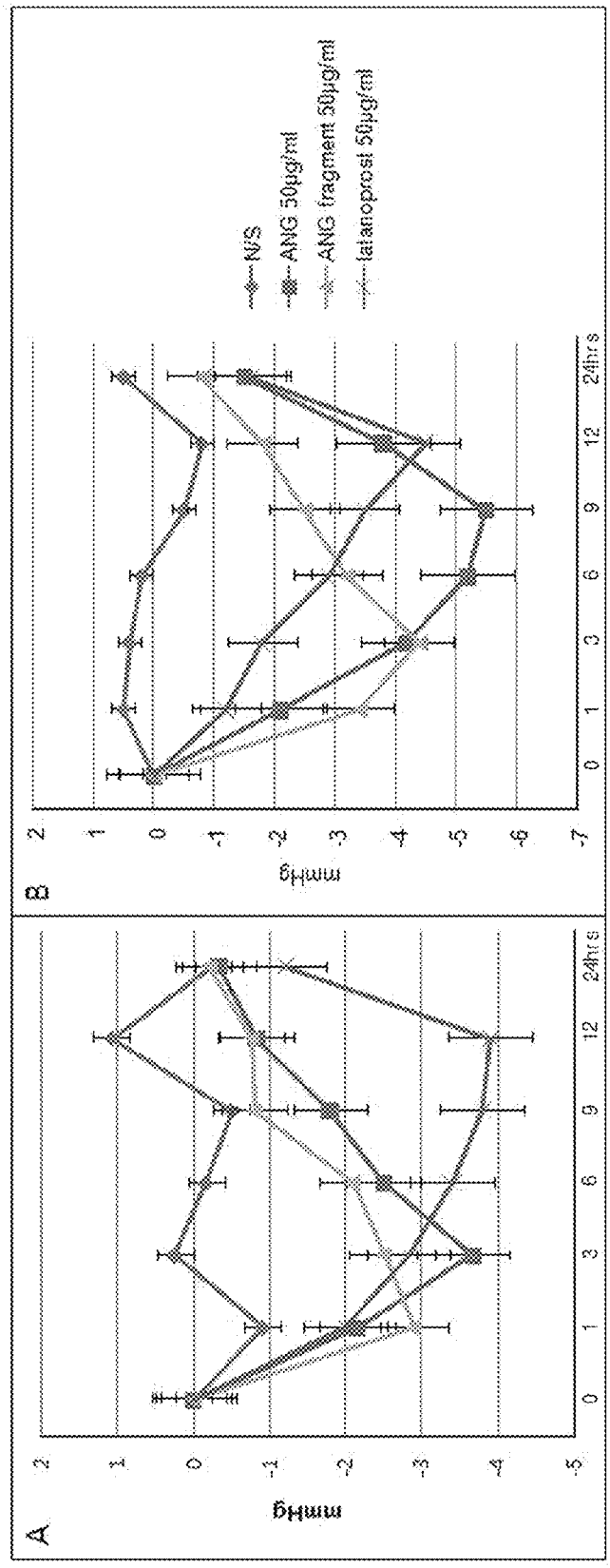
FIG. 3 is a graph of intraocular pressure change of normal rats according to angiogenin instillation. A shows test results of day-time test model, and B shows test results of night-time test model.

FIG. 3 shows test results of normal rats. FIG. 3A shows test results of day-time test model, and FIG. 3B shows test results of night-time test model.

In a day-time instillation test on normal white rat, in which intraocular pressure was calculated based on an assumption that intraocular pressure before instillation is 0, an average intraocular pressure of angiogenin 50 μg/ml instillation group began to significantly decrease 1 hour after the instillation, and up to 9 hours after the instillation, compared to the pre-instillation intraocular pressure, intraocular pressure reduction was maintained at −1.8±0.4 mmHg.

The angiogenin fragment instillation group showed higher intraocular pressure reduction effects than angiogenin instillation. That is, one hour after instillation, the average intraocular pressure reduction was −2.9±0.4 mmHg, and then the intraocular pressure reduction gradually decreased and up to 6 hours after instillation, a significant intraocular pressure reduction was maintained.

The latanoprost 50 μg/ml instillation group showed a significant intraocular pressure reduction of −2.8±0.4 mmHg 3 hours after the instillation, and the significant intraocular pressure reduction effects were maintained up to 12 hours after the instillation. (see FIG. 3A)

In a night-time instillation test on normal white rat, relative intraocular pressure reduction was measured. The angiogenin 50 μg/ml instillation group and the angiogenin fragment instillation group all showed a significant intraocular pressure reduction 1 hour after the instillation, and the angiogenin fragment instillation group showed a higher reduction of −3.4±0.6 mmHg than that of the angiogenin 50 μg/ml instillation group. The angiogenin 50 μg/ml instillation group, compared to that before instillation, maintained the significant intraocular pressure reduction of −1.5±0.4 mmHg up to 24 hours after the instillation, and the angiogenin fragment instillation group maintained the significant intraocular pressure reduction only up to 12 hours after the instillation.

Figure 4:
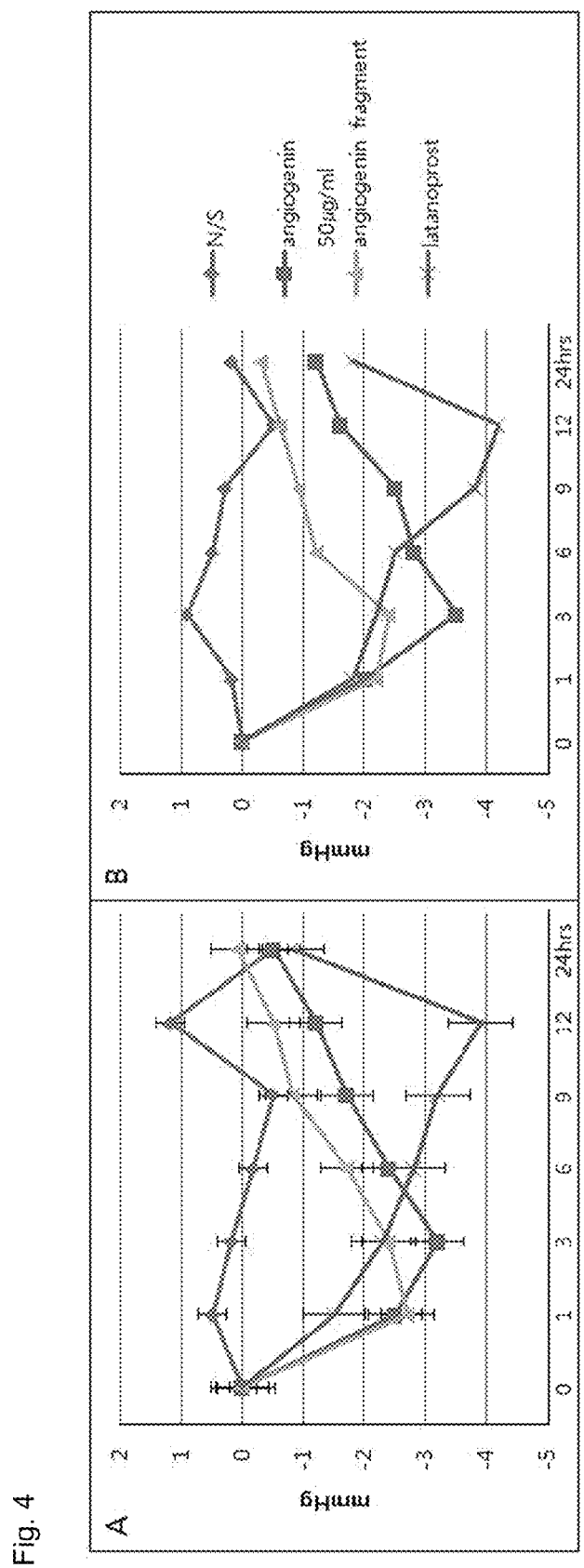
FIG. 4 is a graph of intraocular pressure change of glaucoma white rats according to angiogenin instillation. A shows test results of day-time test model, and B shows test results of night-time test model.

Day-time and night-time instillation test results obtained using glaucoma white rats are shown in FIG. 4. FIG. 4A shows test results of day-time test model, and FIG. 4B shows test results of night-time test model.

Referring to FIG. 4, glaucoma white rats also showed intraocular pressure reduction effects which are similar to those obtained by using normal intraocular pressure rat. In the day-time test and the night-time test, one hour after instillation, the angiogenin fragment showed excellent intraocular pressure reduction effects, and thereafter, the intraocular pressure reduction effects were rapidly diminished at the highest speed from among all of the groups. The angiogenin instillation group retained, during the day-time instillation test, significant intraocular pressure reduction effects up to 6 hours, and during the night-time instillation, retained intraocular pressure reduction effects up to 12 hours after the instillation.

(3) Identification of Intraocular Pressure Change Due to Mixed Administration of Angiogenin and Angiogenin Inhibitory Glaucoma model was grouped as a mixed instillation group of angiogenin and 250 mM neomycin (neomycin sulfate, SantaCruz, USA), which is a nuclear translocation inhibitor of angiogenin, and a mixed instillation group of angiogenin and 0.5 mM PD98059 (PD98059, Biovision, USA), which is a angiogenin ERK pathway inhibitor. Each group consisted of 6 rats, that is, 12 eyes. The mixed installation was performed in an amount of 4 µl, and intraocular pressure was measured before instillation, and 1, 2, 3, 6, 9, 12, and 24 hours after the instillation.

Figure 5:
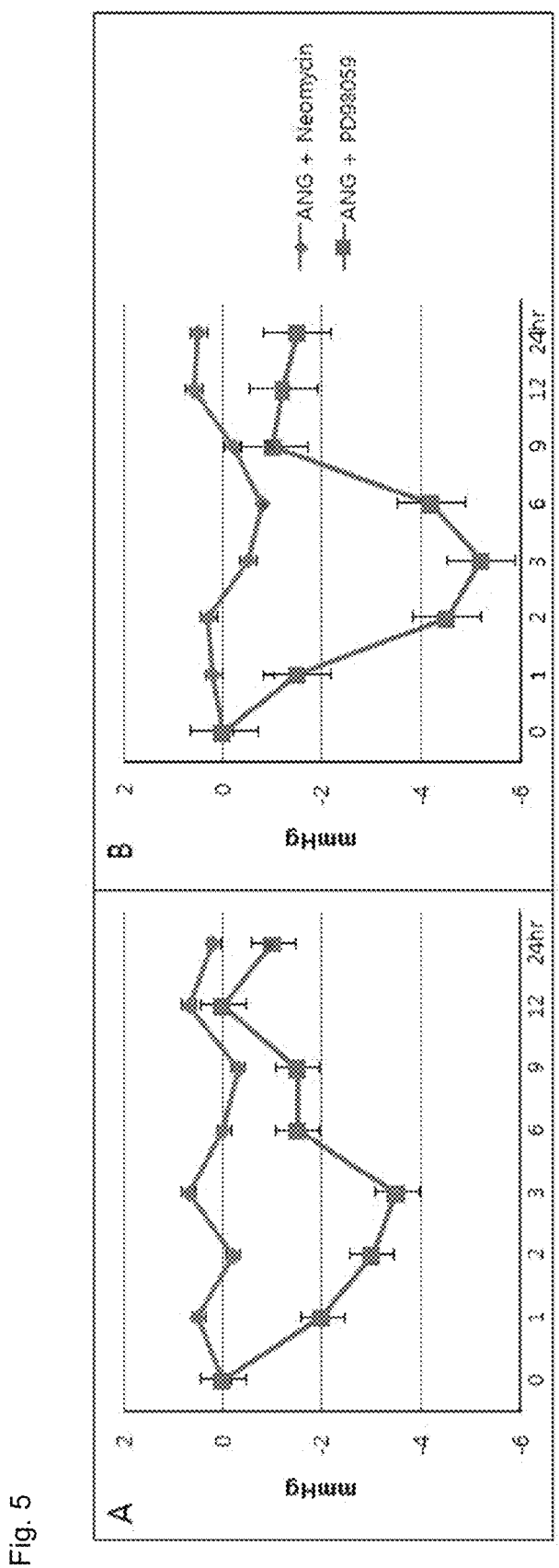
FIG. 5 shows a graph of intraocular pressure with respect to mixed administration of angiogenin and angiogenin inhibitory. A shows test results of episcleral venous ablation glaucoma model, and B shows test results of steroid-induced glaucoma model.

The results are shown in FIG. 5. FIG. 5A shows test results of episcleral venous ablation glaucoma model, and FIG. 5B shows test results of steroid-induced glaucoma model.

Referring to FIG. 5, when angiogenin and neomycin were administered together to episcleral venous ablation glaucoma model and steroid-induced glaucoma model, the two models all did not show a significant intraocular pressure reduction. However, when angiogenin and PD98059 were administered together, the two glaucoma models showed, like the results obtained when only angiogenin was administered, up to 6 hours after instillation, significant intraocular pressure reductions of −1.7±0.3 mmHg and −4.1±0.5 mmHg, respectively.

(4) Immunohistochemical Staining of Rat Model Ocular Anterior Chamber Angle after Angiogenin Instillation Physiological saline solution instillation, angiogenin instillation, mixed instillation of angiogenin and neomycin, and mixed instillation of angiogenin and PD98059 were performed on glaucoma rat model prepared by episcleral venous ablation, and 1 hour after instillation, one eye collected from each group was, in the same way applied to human eyes, subjected to immunohistochemical staining on angiogenin, and observed by microscopy. Results are shown in FIGS. 6 to 8.

Figure 6:
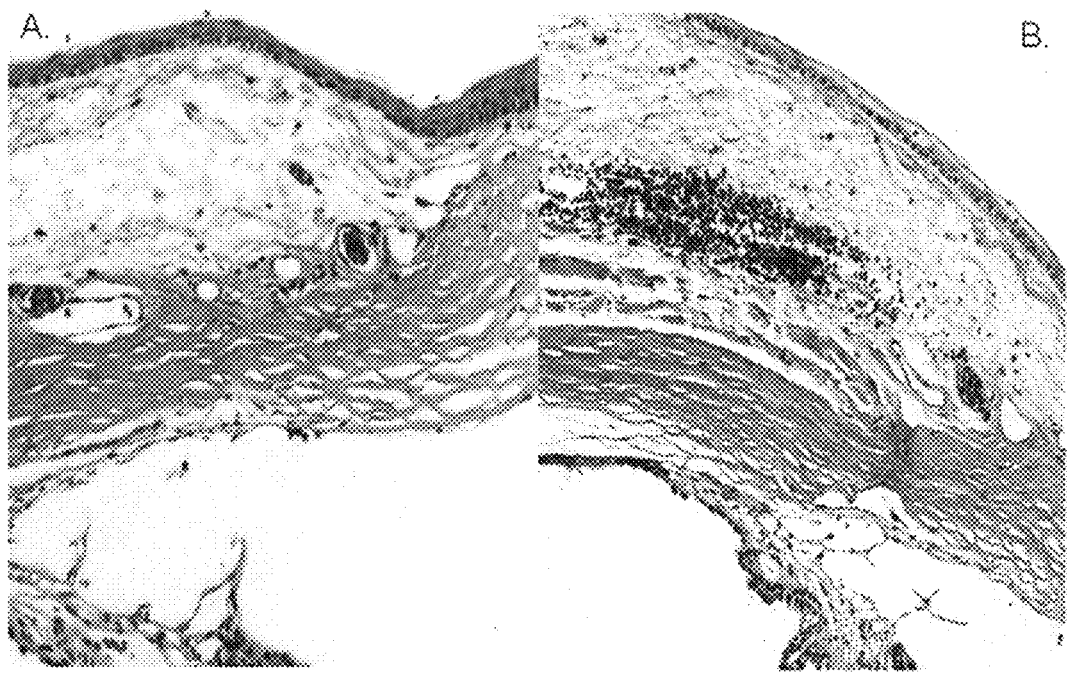
FIG. 6 shows an image of episcleral venous ablation glaucoma model subjected to H&E staining. A shows an image of normal white rat, and B shows an image of episcleral venous ablation glaucoma model.

Referring to FIG. 6, regarding the H&E staining of episcleral venous ablation glaucoma model, compared to normal white rat tissues (A), blood vessel in anterior chamber angle peripheral episcleral had blood congestion due to episcleral venous ablation (B).

Figure 7:
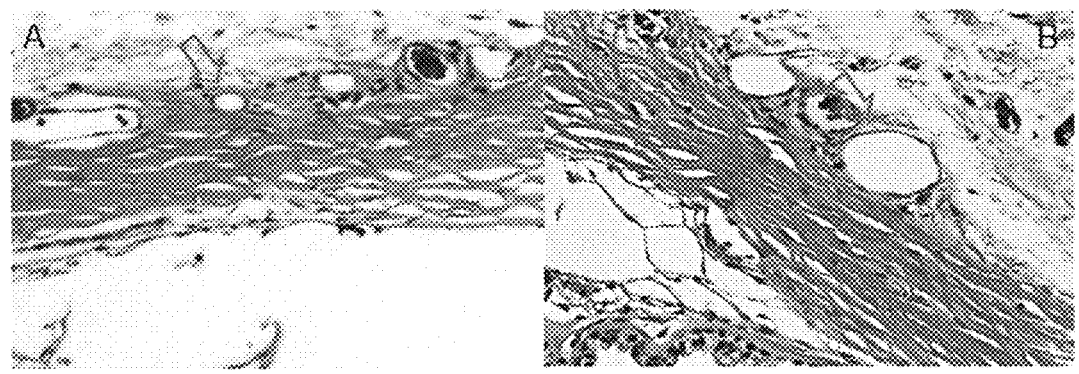
FIG. 7 shows enlarged images of Schlemm's canal peripheral tissue inside anterior chamber angle of glaucoma model subjected to the same ratio of H&E staining before and after angiogenin instillation, respectively.

Referring to FIG. 7 showing enlarged H&E staining images of glaucoma model before instillation (A) and Schlemm's canal peripheral tissue in anterior chamber angle after angiogenin instillation (B), it is confirmed that the diameter and intercellular interval of Schlemm's canal of angiogenin-administered rat were increased after instillation (see the arrow illustrated in FIG. 7).

Figure 8:
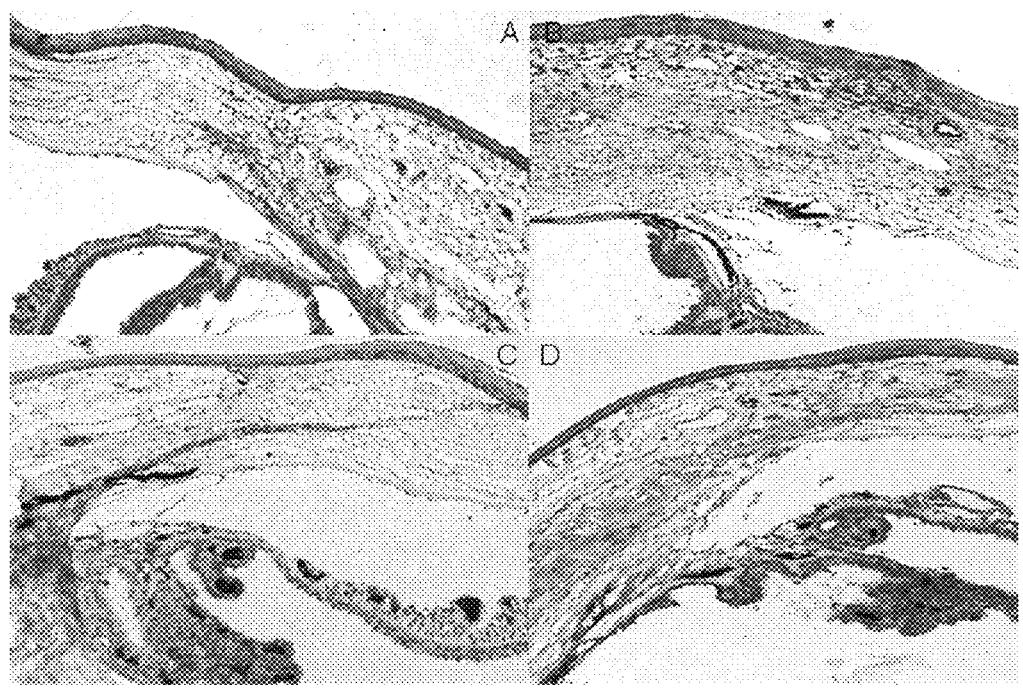
FIG. 8 shows an image of glaucoma model subjected to angiogenin immunospecial staining. A shows an image of glaucoma model before instillation, B shows an image of glaucoma model after angiogenin instillation, C shows an image of glaucoma model after mixed administration of neomycin and angiogenin, and D shows an image of glaucoma model after mixed administration of PD98059 and angiogenin.

Referring to FIG. 8, when the glaucoma model was subjected to angiogenin immunospecial staining, angiogenin stain in anterior chamber angle was intensified (B) compared to that before angiogenin instillation (A), and the same results were obtained even when PD98059 was instilled together (D). However, when neomycin and angiogenin were administered together (C), peripheral angiogenin stain at trabecular meshwork was reduced.

Accordingly, in view that PD98059, which is an Erk route inhibitory, did not suppress angiogenin-derived intraocular pressure reduction, and PI3K and neomycin, which is a nuclear translocation inhibitory, suppressed angiogenin-derived intraocular pressure reduction, it can be confirmed that intraocular pressure reduction mechanism of angiogenin is performed by PI3K, which is a NO formation route, and a nuclear translocation, that is, by a final product NO. This is supported by test results obtained in Example 3.

<Example 3> NO Concentration Change in Normal and Glaucoma Rat Model Aqueous Humor after Angiogenin Instillation Normal rat models were divided into 4 groups, each group consisting of 6 rats, that is, 12 eyes, and at 8 AM and 8 PM, each group was instilled with angiogenin 50 µg/ml, angiogenin fragment 50 µg/ml, and latanoprost 50 µg/ml, and 1, 3, and 6 hours after instillation, 15 to 20 µl of aqueous humor was extracted from two rats, that is, 4 eyes for each group. For the extraction of aqueous humor, first, rats were anesthetized, and then, corneal dissection was performed in a direction from at 9 o'clock outside each eye toward microkeratome, and then, a capillary tube was brought into contact through a dissection wound to absorb aqueous humor, which was then moved to an eppendroff tube and frozen-preserved at a temperature of −70 degrees. Thereafter, nitric oxide (NO) concentration in aqueous humor was measured by Griess assay (nitric oxide colorimetric assay kit, Biovision, USA). The aqueous humor was diluted 10 times and then mixed with the same amount of griess solution and reacted together for 10 minutes. The reaction product was moved onto a well plate and then, absorbance of nitrate, which is a NO formation reactant, was measured by using spectrophotometer at a wavelength of 540 nm and compared with a reference value to quantify the nitrate.

Figure 9:
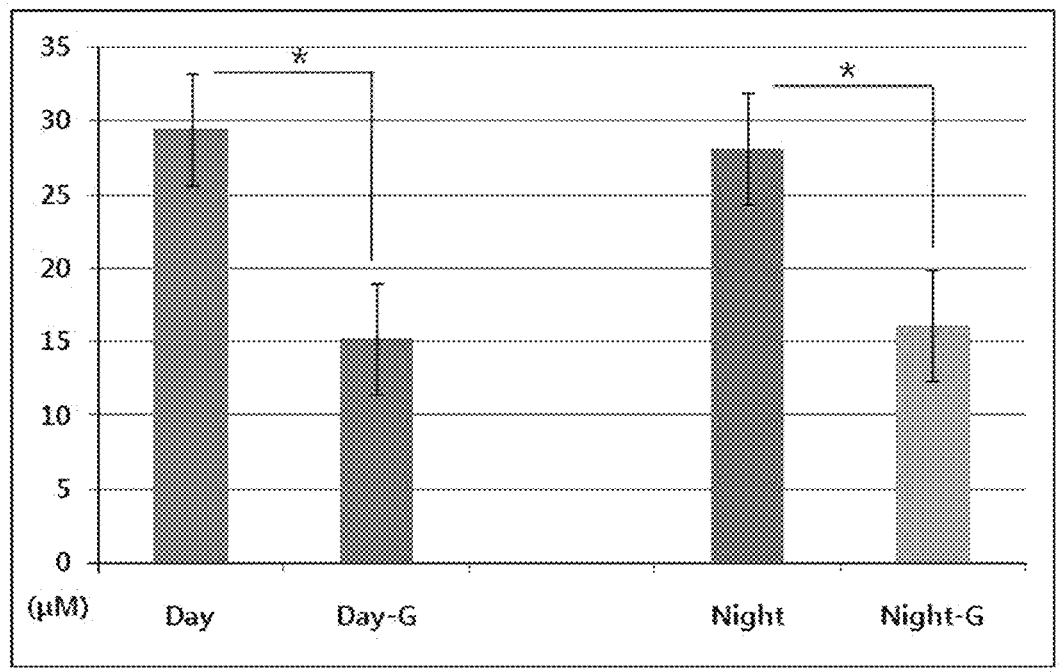
FIG. 9 shows a graph of NO concentration in aqueous humor of normal rat with respect to angiogenin instillation.

Referring to FIG. 9, in the case of normal rats, NO concentration in aqueous humor during day-time was not different from that during night-time. However, during day-time and night-time, NO in aqueous humor of normal rats was significantly different from that of glaucoma model rat. That is, average NO concentration in aqueous humor of glaucoma model rats during day-time and night-time were 15.1±3.7 µM and 16.5±3.5 µM, respectively, which were statistically, significantly lower than NO concentrations in aqueous humor of normal rats: 29.1±4.5 µM and 27.5±5.1 µM.

Figure 10:
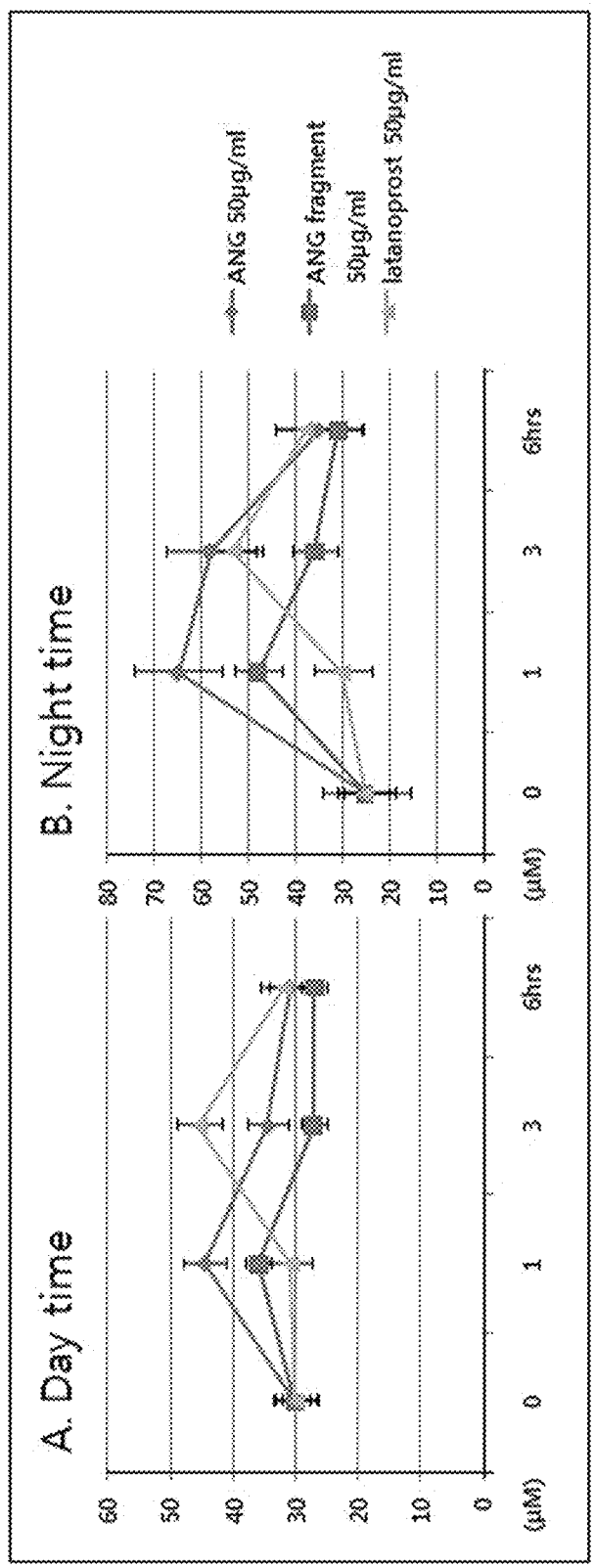
FIG. 10 shows a graph of NO concentration in aqueous humor of glaucoma model with respect to angiogenin instillation.

Referring to FIG. 10, NO concentration in aqueous humor assay performed on the normal glaucoma model before and after instillation shows that the instillation groups showed similar results in the day-time test and the night-time test. That is, the two tests commonly showed that angiogenin showed the greatest NO concentration increase 1 hour after the initial instillation, and angiogenin fragment ranked the second in terms of the initial NO concentration increase. 3 hours after instillation, the latanoprost instillation group showed the greatest NO concentration increase. Compared to the day-time test group, the night-time test showed greater NO concentration increase.

<Example 4> Angiogenin Concentration Change in Human Tear after Long-Term and Short-Term Latanoprost Instillation Angiogenin concentration change in tears due to long-, short-term instillation of 0.0005% Latanoprost (Xalatan; Pfizer Inc., New York, N.Y., USA) was assayed by using ELISA kit (Custom Cytokine Human Antibody Array, RayBiotech). Short-term tear component change assay was performed as follows: 12 people, that is, 24 eyes were instilled with 0.0005% Latanoprost and then, angiogenin concentration in tear was qualitatively assayed before instillation and 6 hours after instillation. Long-term tear component change assay was performed as follows: 10 people, that is, 20 eyes, who were newly diagnosed with glaucoma were instilled with 0.0005% Latanoprost instillation for two months once a day, and then, angiogenin concentration in tear was analyzed before and after instillation. 30 µL or more of tear was obtained from a lower conjunctival fold of a patient by using glass capillary (Marienfeld, Lauda-Konigshofen, Germany) having a diameter of 10 µL while minimizing stimuli as much as possible, and then, the tear was collected in a microtube and preserved at a temperature of −70° C. for assay purpose. The angiogenin concentration assay was performed as follows: an ELISA array kit containing angiogenin antibody doubly aligning in the form of spot on a membrane was treated with a buffer solution provided by a manufacturer, and then, human tear was placed thereon, and then, reacted with secondary antibody with biotin attached thereto at room temperature for 1 hour, and the result was washed and reacted with streptavidine with horseradish peroxidase (HRP) attached thereto for 1 hour at room temperature. After washing, the result was reacted in a detection buffer solution provided by the manufacturer for 2 minutes, and then, the membrane was exposed to an X-ray film for 40 seconds, and an image thereof was obtained by using Quantity one software(Bio-Rad Lab., Hercules, Calif., USA), and chemiluminescent assay was performed thereon for qualitativeness.

Figure 11:
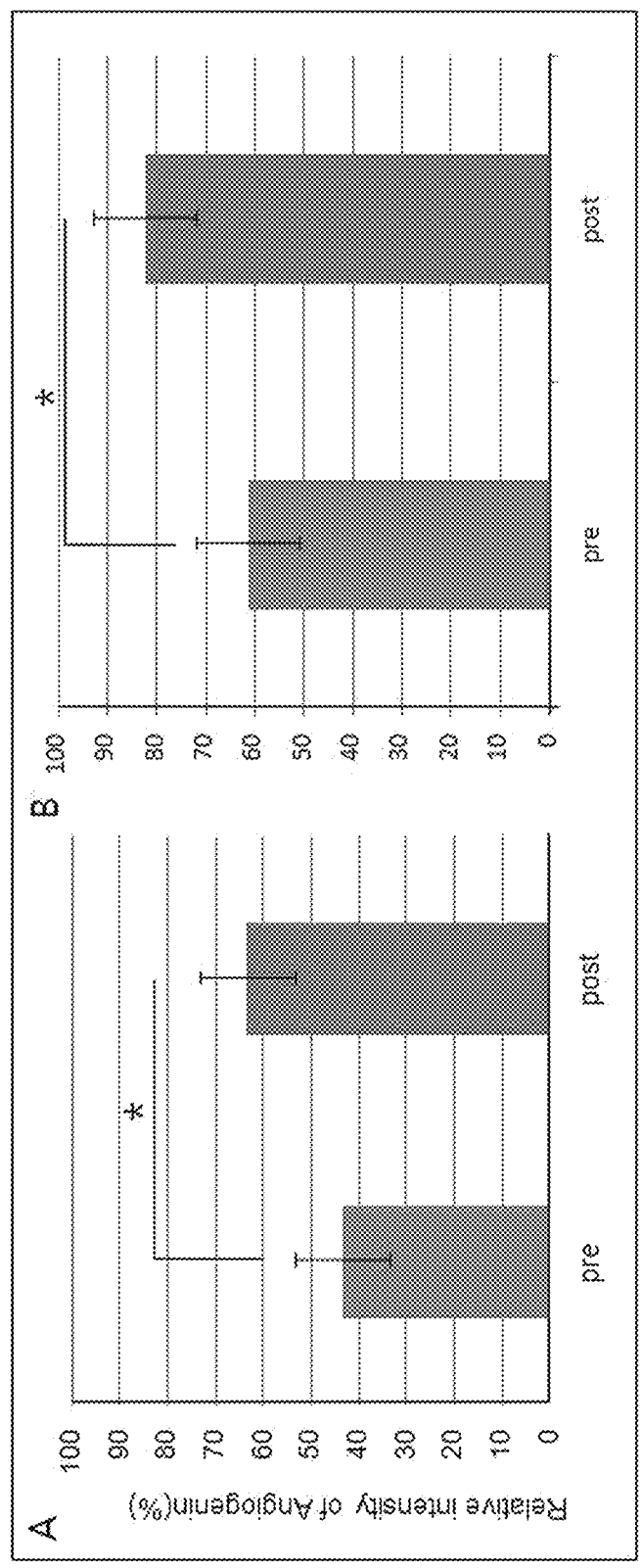
FIG. 11 shows a graph showing a short-term angiogenin concentration change in tears after Latanoprost instillation. A shows short-term test results, and B shows long-term test results.

FIG. 11 shows short-term angiogenin concentration change in tear after Latanoprost instillation. FIG. 11A shows short-term test results and FIG. 11B shows long-term test results. Referring to FIG. 11, compared to that before instillation, 6 hours after instillation, expression of angiogenin in tear was significantly increased from 42.2±9.1% to 62.5±10.2%. After two months of instillation with Latanorprost, long-term angiogenin concentration in tear was significantly increased from 60.5±10.8%, which was a value before instillation, to 81.2±11.5%.

Experimental Example

The following experimental examples are commonly applied to Examples provided herein.

1.1. Subject Test Rat (Rat)

Rats (Sprague-Dawley species, male) raised at the clinic research center of College of Medicine of Chung-Ang University were used as a test animal. 8-week twenty rats had an average weight of 260 g (250 to 270 g). The breeding room for the test animal had a temperature of 22 to 25° C., and a relative humidity of 50 to 60%, and darkness thereof was automatically controlled.

2. Preparation of Chronic Intraocular Pressure Increase Model and Measurement of Intraocular Pressure 0.05 cc/50 g of Tiletimine and Zolazepam-mixed medicament (Zoletil) and Xylazine (Rompum) were mixed at a ratio of 1:1 and then administered to 20 rats by intramuscular injection, thereby anesthetizing the rats. A limbus periphery was divided into four portions, each of which was then subjected to 2 mm dissection at an interval of 90 degrees, and then, two radial conjunctival excisions were performed on upper dissection periphery. Tissue was pushed backward to make extra ocular muscle to be exposed and then, two back-side episcleral veins near superior rectus muscle and one ear-side episcleral vein near lateral rectus muscle were separated. After surgical isolation of vein, the vein was lifted up by using 3 mm-width spatula to be spaced apart from the peripheral tissue, and then, was subjected to electric ablation while being careful for the peripheral tissue not to have any thermal damage or any mechanical damage due to contact. Intraocular pressure was consecutively measured three or more times by using Tonopen (Solan, Fla., USA), and only reliable intraocular pressure values within 5 percentile were recorded. 10 eyes of 10 rats were daily treated 4 times with angiogenin 10 µl 2 days before test, and even after espisderal venous electric ablation, 4 times a day at time intervals of 6 hours. The other 10 eyes of the rats, as a control, were consecutively treated in the same manner with physiological saline solution 10 µl before and after the ablation. Before the operation, and 3 days, and 1, 2, 4, and 8 weeks after the operation, intraocular pressure was measured, and the rats were sacrificed to extract eyes therefrom, which were then subjected to tissue examination and immunechemical staining with respect to Brn-3a and CD11b, and a reverse transcription polymerase chain reaction was used to measure CD11b value in retinal tissue.

3.3. Tissue Section Preparation and Immunohistochemical Staining

After pre-fixing with 4% paraformaldehyde solution, tissue was treated with paraffin to form a paraffin block. Then, the tissue was cut to obtain a tissue section, which was then attached onto a slide glass. Paraffin was removed by using Dewaxing solution and then, the result was repeatedly treated twice with alcohol. The tissue section was treated with 1% Triton X-100 for 10 minutes, and then, three times with PBS each for 10 minutes. The result was blocked with Normal donkey serum (Vector, Calif., USA) for 1 hour, and then, reacted with 0.1% triton X-100—containing primary antibody mouse anti-NR1 (1:500), mouse anti-GluR2/4 (1:1000), rabbit anti-GluR6/7 (1:000), and rabbit antimGluR6(1:10000) at a temperature of 4° C. for one day. The tissue was washed three times with PBS each for 10 minutes, and then, treated with secondary antibody goat anti-rabbit- or anti-mouse-rhodamine (SantaCruz, Calif., USA) together with 0.1% triton X-100 at a temperature of 4° C. for two hours. After the treatment with secondary antibody, the tissue was washed three times with PBS each for 10 minutes. Brn-3a, which is used for staining retinal ganglioncell, and CD11b, which is used for staining a macrophage derived from monocyte, were used as a primary antibody during staining.

4. Corneal Chemical Burn Model Preparation and Anterior Ocular Segment Photographing Regarding 20 eyes of 20 rats, filter paper was cut to a round shape having a diameter of 4 mm and completely wet with NaOH, and then, placed on corneal and conjunctiva with upper corneal limbus therebetween for 6 seconds, and then, the eyes were washed. 10 eyes of the 10 rats were treated with angiogenin 10 µl four times a day at time intervals of 6 hours two days before test, and even after the NaOH injury, treated 4 times a day. The remaining 10 eyes were treated with physiological saline two days before the injury in the same manner as used with angiogenin. Angiogenin and physiological saline were all administered only up to 7 days after injuring.

Three days, and 1, 2, 4, and 8 weeks after injuring, corneal opacity and neoangiogenesis level were assessed in consideration of images of anterior ocular segment, and on the third day and the seventh day, the respective conjunctiva damaged parts were collected and then subjected to a reverse transcription polymerase chain reaction to assay expression of IL-1a, TGF-β, SDF-1, and caspase-3.

According to the classification method suggested by Sonoda and Streilein, corneal opacity is scaled in four grades: grade 0 indicates completely transparent cornea; grade 1 indicates slight opacity in which iris is completely shown; grade 2 indicates moderate opacity in which iris vessel is shown; grade 3 indicates intermediate corneal opacity in which pupillary margin is shown but iris vessel is not shown; and grade 4 indicates complete corneal opacity in which pupillary margin is not shown.

On the corneal neoangiogenesis image, the region where blood vessel was grown was divided in the wedge shape at intervals of 1 hour while the corneal peak was used as a reference, and an area thereof was calculated, and the area was calculated according to this equation: $A=C/12\times 3.1416 [r^2-(r-1)^2]$. (A: new vessel area, C: time occupied when divided by 12 hours, r: corneal diameter, and l: vascular grown length)

5. Semi-Quantitative Assay Using Reverse Transcription Polymerase Chain Reaction Tissues obtained from chronic intraocular pressure increase model and corneal chemical burn model were frozen, and then cut into small parts by using a fine knife. The tissue parts were treated with 1 ml of TRI reagent (Molecular Research Center, Inc.) and then, tissue and cell were lysed by homogenizer. The respective implication cDNA 0.6 1 0.2 mM dNTP, 10×buffer, 10 pmols primer, and 0.2 U Taq polymerase were mixed to obtain a volume of 20 µl, and then, PCR thermal cycler (a machine for PCR) was used for reaction for 5 minutes at 95° C., 40 second at 94° C., 40 seconds at 48 to 64° C., 40 seconds (35 cycles) at 72° C., and 10 minutes at 72° C. The amplified polymerase chain reaction product was identified by 1% agarose gel electrophoresis. β actin was used as a positive control for the polymerase chain reaction, and relative expression morphs of a target gene with respect to β actin expression were compared. In the case of rat retinal tissue of chronic intraocular pressure increase model, CD11b, which is a macrophage marker derived from monocyte, was assayed, and in the case of rat conjunctiva tissue of corneal chemical burn model, IL-1a, TGF-β, SDF-1, and caspase-3 were assayed.

Figure 12:
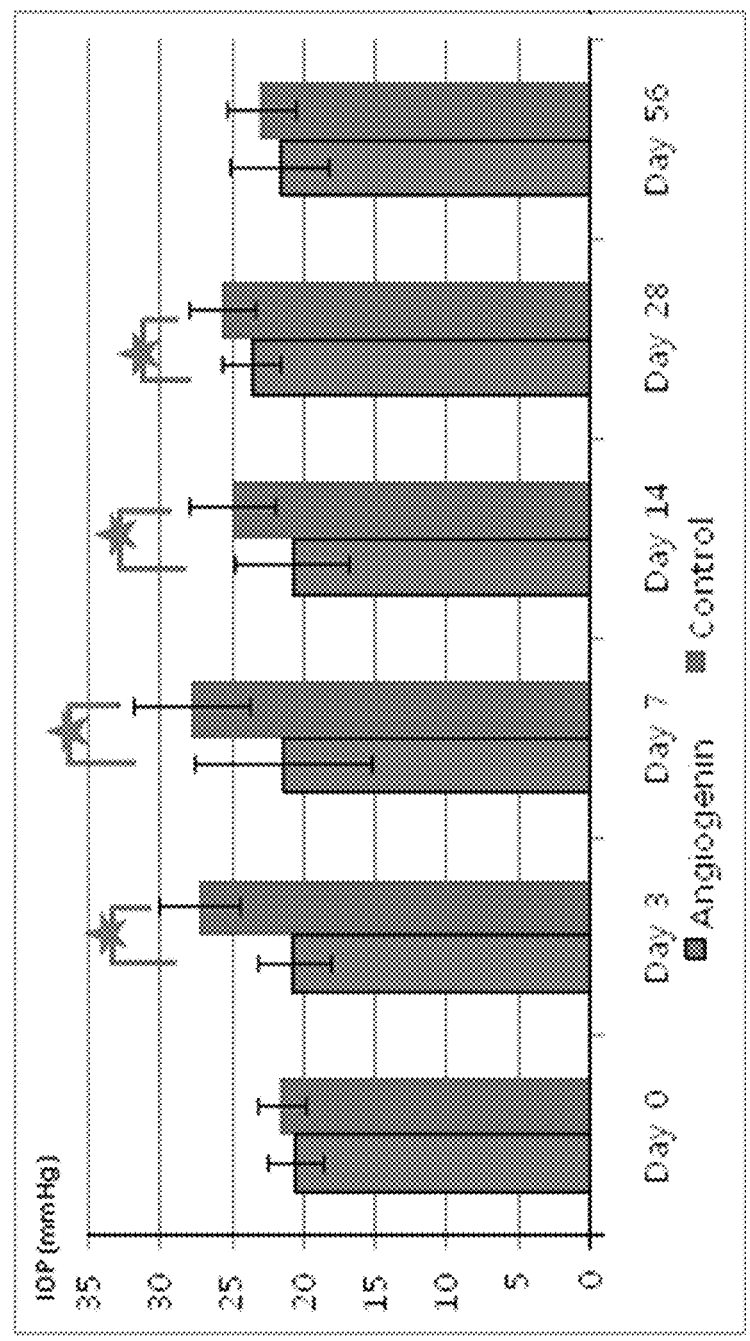
FIG. 12 shows intraocular pressure reduction effects of angiogenin on rat model with increased chronic intraocular pressure.

<Example 5> Intraocular Pressure Reduction Effects of Angiogenin on Chronic Intraocular Pressure Increase Rat Model Before test, an average intraocular pressure of 10 eyes of angiogenin treated group rats was 20.6±1.9 mmHg, and an average intraocular pressure of 10 eyes of angiogenin untreated group rats was 21.6±1.8 mmHg. That is, intraocular pressure of the two groups did not have a significant difference. For 8 weeks, an average intraocular pressure of the angiogenin treated group was 21.2±3.8 mmHg, and that of the control was 25.4±3.6 mmHg. Three days, and 1, 2, 4, and 8 weeks after the treatment, an average intraocular pressure of the angiogenin treated group was 20.7±2.6 mmHg, 21.4±6.2 mmHg, 20.8±4.0 mmHg, 23.6±2.0 mmHg, and 21.7±3.4 mmHg, respectively, and that of the control was 27.3±2.9 mmHg, 27.8±4.1 mmHg, 25±3.0 mmHg, 25.6±1.6 mmHg, and 23.0±2.4 mmHg, respectively. Results are show in FIG. 12.

Referring to FIG. 1, 3 days, and 1, 2, and 4 weeks after the episcleral venous injury, an average intraocular pressure of the angiogenin treated group was significantly lower than that of the control, and on the third day after the treatment, the intraocular pressure difference was the biggest: 6.75±0.3 mmHg.

<Example 6> Ganglion Cell Protection Effects of Angiogenin Treatment on Chronic Intraocular Pressure Increase Model On H-E staining of rat tissue obtained from chronic intraocular pressure increase model by episcleral venous electric ablation, density of retinal ganglion cell located above retina was assayed. Results are shown in FIGS. 13 and 14.

Figure 13:
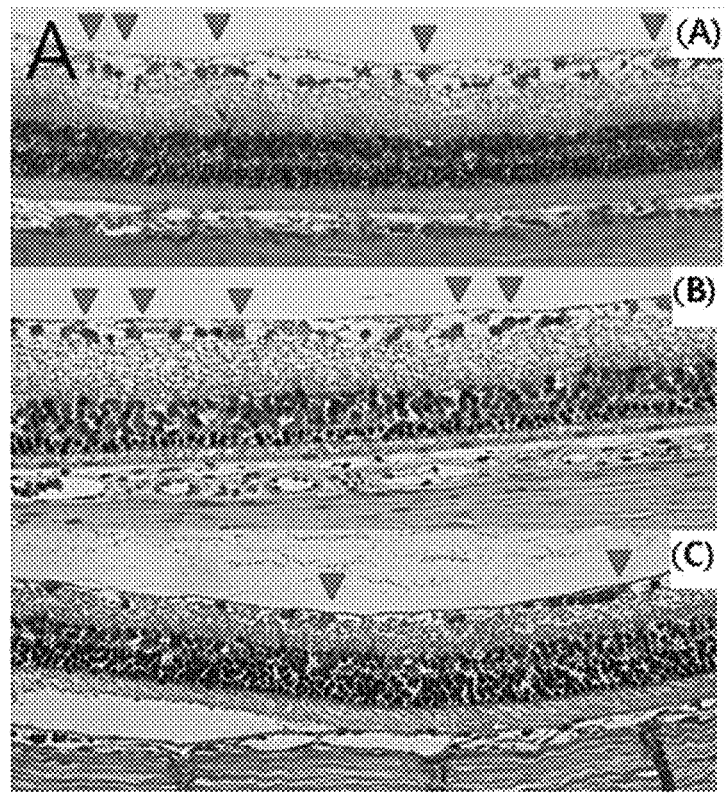
FIGS. 13 and 14 are images showing retinal ganglion cell density of rat model with increased chronic intraocular pressure. (A) shows an image of a general retinal cell, (B) shows an image of angiogenin treated group, and (C) shows an image of control which is not treated with angiogenin.

FIG. 13A is an image of normal retinal cell, FIG. 13B is an image of angiogenin treated group, and FIG. 13C is an image of angiogenin untreated control. Referring to FIG. 13, 8 weeks after the injury, the retinal thickness and the retinal ganglion cell density of the control (C) are substantially lower than those of normal rat (A), and in the case of angiogenin treated group (B), the density of retinal ganglion cell does not change.

Figure 14:
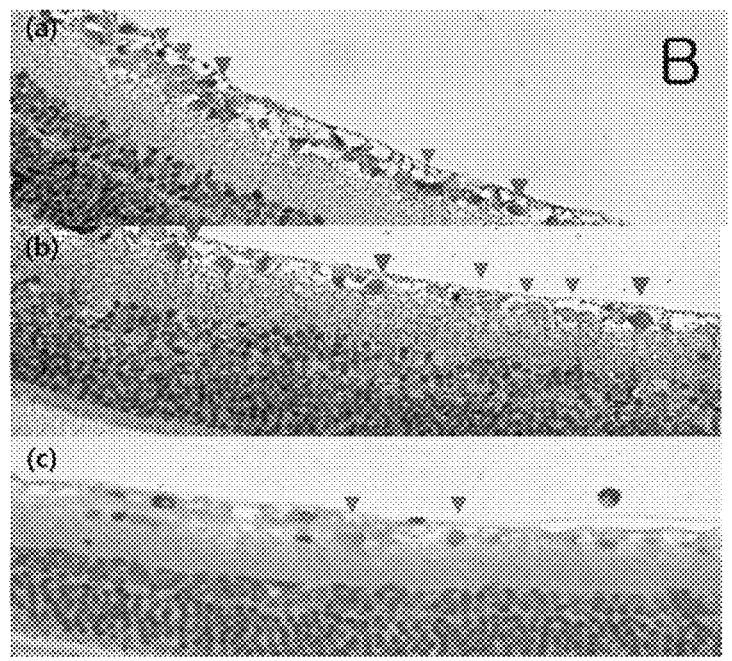

FIG. 14 shows immunochemical staining results of retinal ganglion cell. FIG. 14A shows Brn-3a, FIG. 14B shows CD11b, and FIG. 14C shows a control.

On immunochemical staining, in the control, the density of Brn-3a marked retinal ganglion cell was substantially decreased (c); in the angiogenin-treated group, the density of Brn-3a marked retinal ganglion cell was well maintained (a); and CD11b marked macrophage was highly frequently distributed in a retinal ganglion layer (b).

Figure 15:
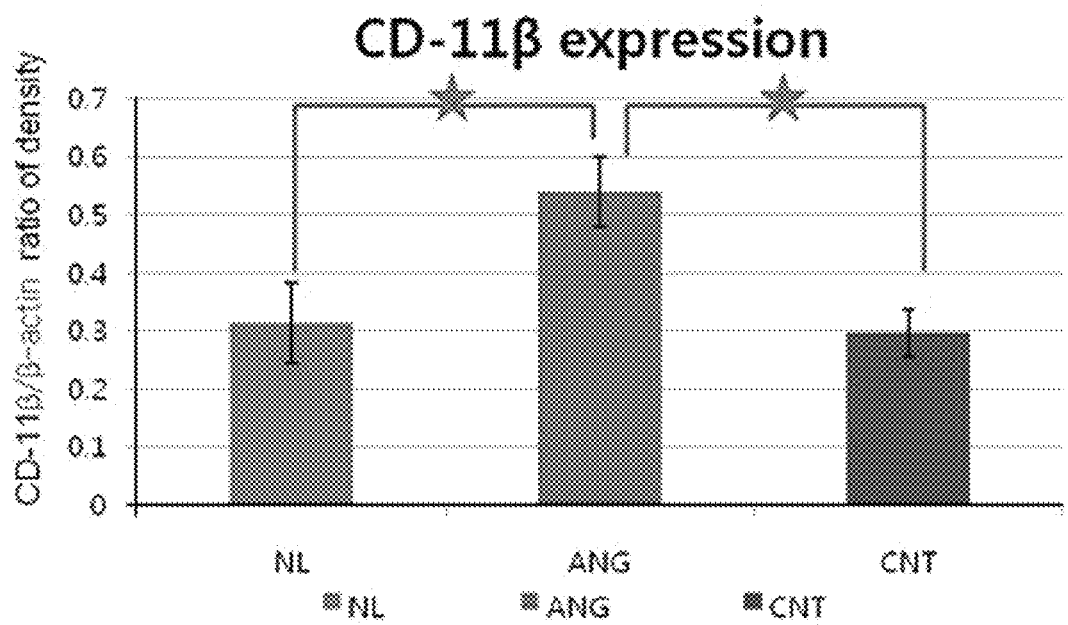
FIG. 15 shows results of a reverse transcription polymerase enzyme chain reaction performed on retinal tissue isolated from rat eyeball on the seventh day after espisderal venous electric ablation.

FIG. 15 shows results of a reverse transcription polymerase chain reaction performed on retinal tissue isolated from eyes of rats on the seventh day after episcleral venous electric ablation. Referring to FIG. 15, the angiogenin treated group showed a significantly higher CD11b expression in retina than the control and the normal rat group.

A recent paper disclosed that in the rat retinal model injured due to glutamate intravitreal injection or intraocular pressure increase, a macrophage derived from monocyte is infiltrated into the rat's injured retinal to increase the survival of retinal ganglion cell and to cause retinal progenital cell renewal. These effects may be due to IL-10 and MHC-II secreted by macrophage.

Accordingly, in light of higher levels of CD11b, which is a macrophage marker derived from monocyte, in the angiogenin-treated group than in the control on polymerase chain reaction results, and the small decrease in ganglion cell number, it is assumed that intraocular pressure reduction effects and neuroprotective effects of angiogenin may be associated with action of monocyte-derived macrophage. Angiogenin may act as a chemotactic factor to promote gathering of monocytes in aqueous humor outflow channel in retina in blood vessels, and the activated macrophage prevents apoptosis of retinal ganglion cells, and increase the flow of aqueous humor outflow channel.

<Example 7> Identification of Anti-Inflammatory Effects of Angiogenin on Corneal Chemical Burn Model The inventors of the present invention confirmed that angiogenin suppresses corneal opacity and corneal neoangiogenesis in the corneal chemical burn model.

Figure 16:
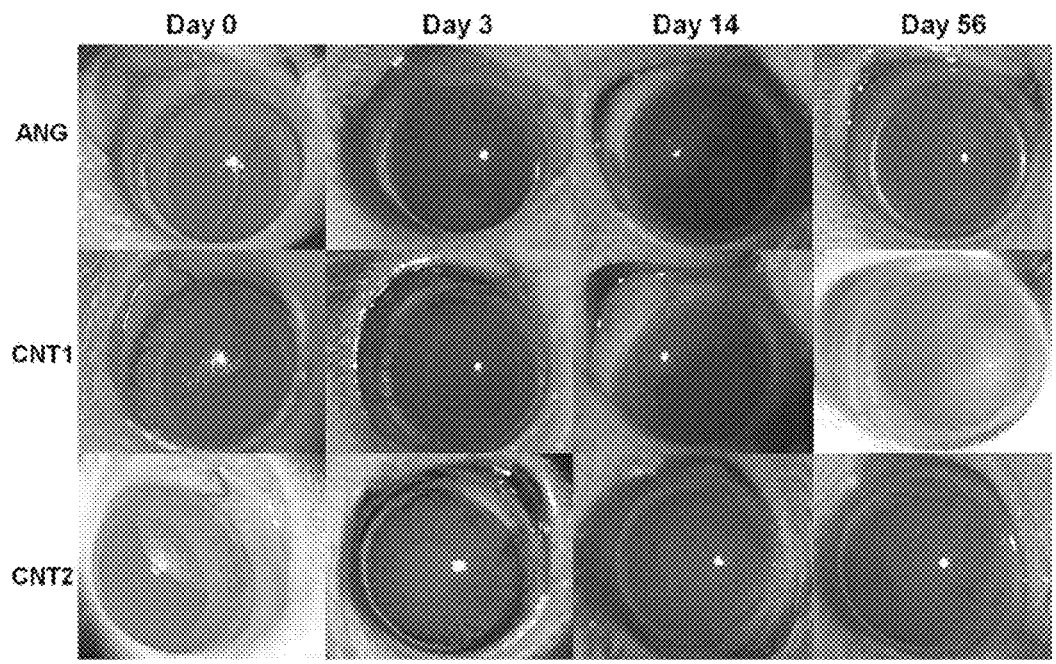
FIGS. 16 to 18 show test results obtained from images of anterior ocular segment of corneal chemical burn model.
Figure 17:
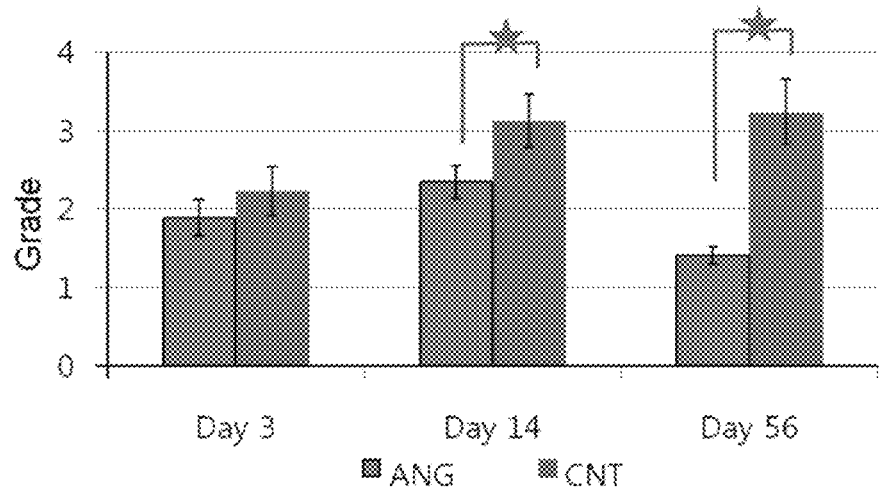
Figure 18:
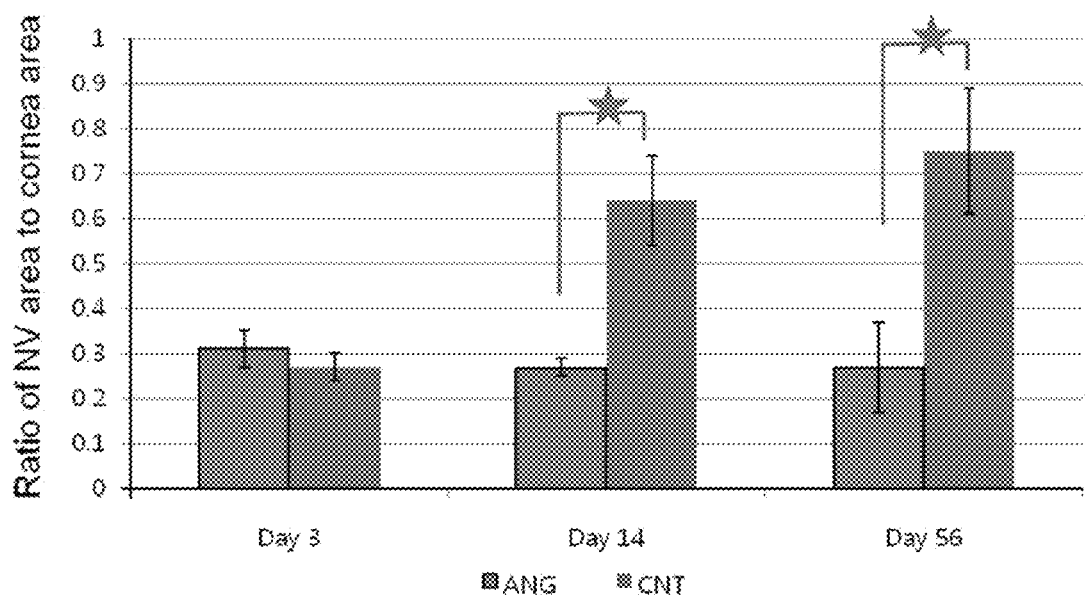

The corneal opacity suppression was confirmed by referring to anterior ocular segment photographs, and results thereof are shown in FIGS. 16 to 18. FIG. 16 shows images of anterior ocular segments, FIG. 17 is a graph of grades determined in view of the images, and FIG. 18 is a graph of a corneal new vessel area calculated.

Referring to FIGS. 16 to 18, on the anterior ocular segment images, the third day after the injuring of keratoconjunctiva, the angiogenin treated group and the control had ischemic corneal limbus, and compared to the angiogenin treated group, the control showed serious ischemia, serious inflammatory secretions, and partial necrosis. As for corneal opacity, up to the seventh day, the two groups had no significant difference. However, from 2 weeks after the injury to 8 weeks, compared to the control, the angiogenin treated group showed a significantly low corneal opacity, and the most of the group had grade 1 or grade 2 (see FIGS. 16 and 17). However, the control showed that 7 days after the injury, most rats continuously developed opacity and neoangiogenesis during test.

As for corneal neoangiogenesis, on the initial third day, the two groups all developed corneal new vessels. However, on the second week, the two groups showed a stark difference, and in the angiogenin-treated group, the corneal new vessel area did not change. From among corneal opacity formed up to the initial seventh day, opacity of a part that did not accompany corneal neoangiogenesis became weak or disappeared, and opacity of a part that did accompany corneal neoangiogenesis gradually became serious (see FIGS. 16 and 18).

In the two groups, the opacity of a part that did not accompany corneal neoangiogenesis from among corneal opacity formed up to the initial seventh day may be developed due to temporary corneal edema and inflammatory reaction between inflammatory cells and an inflammatory material, and on week 4, the opacity became mostly weak or disappeared; and the opacity of a part that did accompany corneal neoangiogenesis gradually became serious.

During this test, angiogenin was administered only from 2 days before the corneal injury up to the seventh day after the injury. This was intended to reduce inflammatory response in the procedure of initial wound treatment so that destruction of secondary corneal matrix is prevented and during post re-regeneration, promotion of corneal neoangiogenesis is prevented.

From among these materials, TGF-β induces activation and differentiation of corneal parenchyma fibroblast, apoptosis, and fibrosis during wound treatment, thereby acting as a major cause of corneal opacity. Also, stromal cell-derived factor-1 (SDF-1) is a chemotactic factor belonging to CXC family, and plays a critical role in angiogenesis due to its chemotaxis function with respect to inflammatory cells, such as lymphocyte, and endothelial recruiting through an action mechanism of endothelial progenitor cell from bone marrow through CXCR4. SDF-1 is also known as being associated with metastasis of tumor, such as breast cancer. Also, Caspase-3 is a marker for apoptosis.

During test, in the injured tissue collected on the third day and seventh day after keratoconjunctival chemistry injury, the angiogenin treated group showed low levels of IL-1a, TGF-β, SDF-1, and caspase-3. Accordingly, it is assumed that due to immunological action of angiogenin, IL-1a, which is an inflammatory cytokine, is suppressed; TGF-β, which induces corneal opacity and fibrosis, is suppressed; SDF-1, which is an immune control material causing angiogenesis, is suppressed; and caspase-3, which is a marker of inflammation and apoptosis, is suppressed, so that inflammation is reduced and corneal opacity and corneal neoangiogenesis are suppressed.

It should be understood that the exemplary embodiments described therein should be considered in a descriptive sense only and not for purposes of limitation, and do not limit the scope of the present invention. Accordingly, the substantial scope of the present invention is defined by the following claims and equivalents thereto.

```
                        SEQUENCE LISTING

<160> NUMBER OF SEQ ID NOS: 1

<210> SEQ ID NO 1
<211> LENGTH: 15
<212> TYPE: PRT
<213> ORGANISM: Homo sapiens

<400> SEQUENCE: 1

Glu Asn Gly Leu Pro Val His Leu Asp Gln Ser Ile Phe Arg Arg
1               5                   10                  15
```

Figure 19:
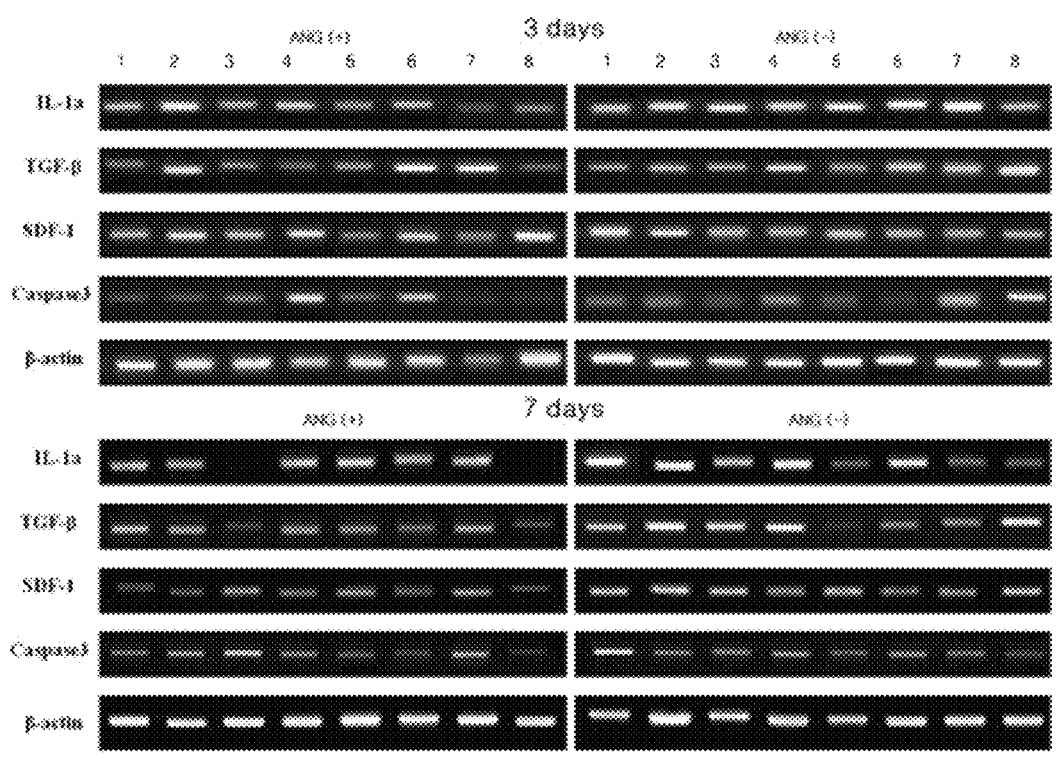
FIGS. 19 to 21 show a graph showing results of reverse transcription polymerase chain reaction performed on injured tissue on the third day and the seventh day after keratoconjunctival chemical injury.
Figure 20:
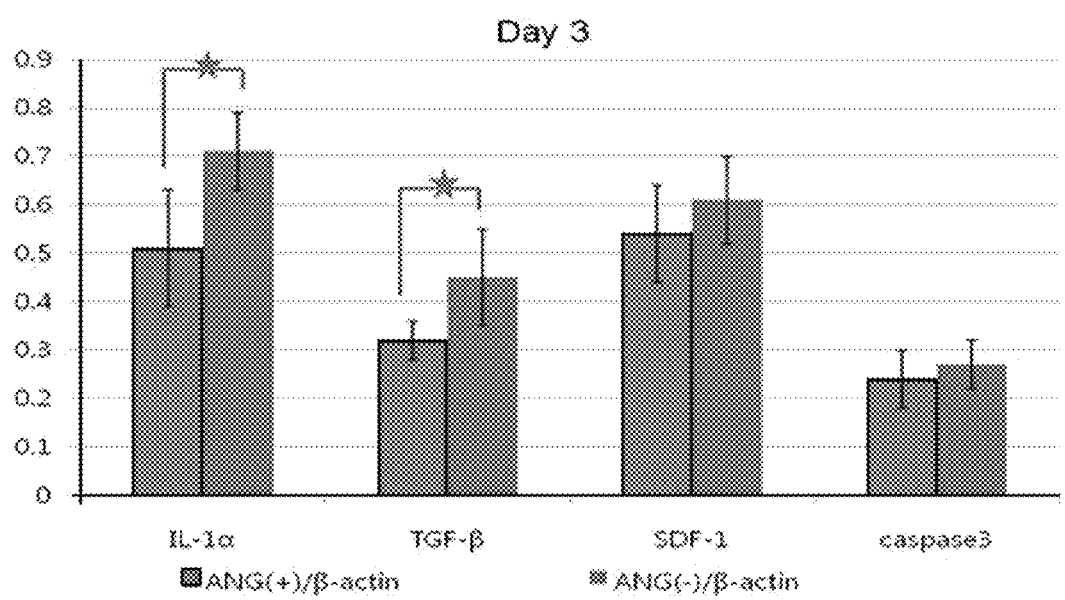
Figure 21:
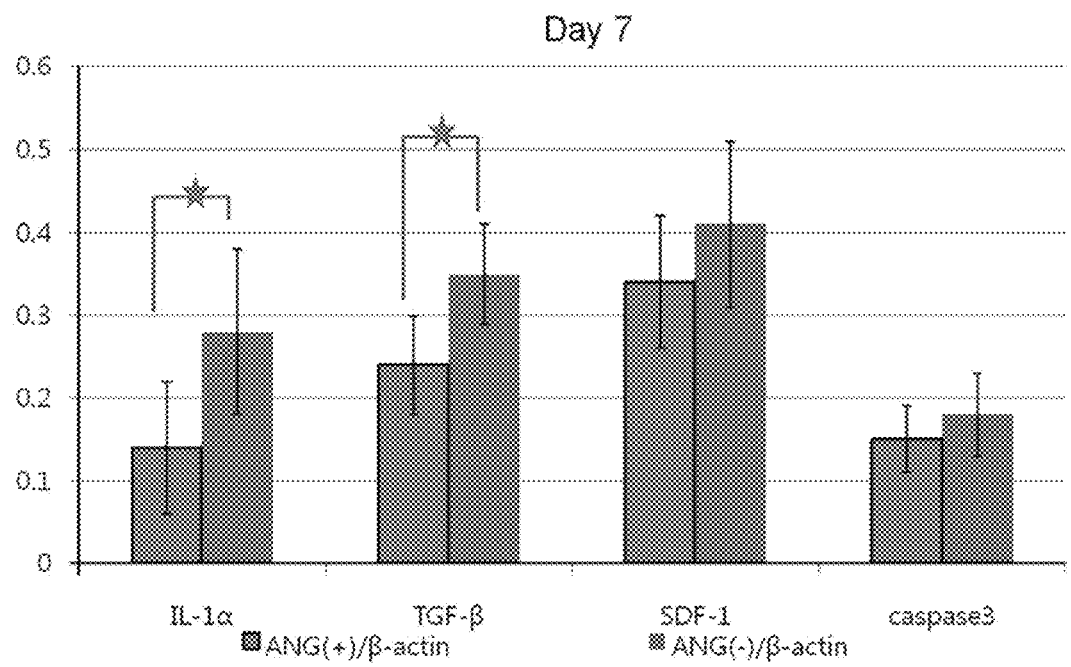

FIGS. 19 and 21 show results of reverse transcription polymerase chain reaction performed on injured tissue collected on the third day and the seventh day after keratoconjunctival chemistry injury. FIG. 19 shows an image showing test results of reverse transcription polymerase chain reaction, FIG. 20 is a graph of results obtained on the third day after injuring, and FIG. 21 is a graph of results obtained on the seventh day after injuring.

Referring to FIGS. 19 to 21, IL-1a, TGF-β, SDF-1, and caspase-3 were all less expressed in the angiogenin treated group than in the control.

Generally, corneal chemical burn causes corneal limbus cell depletion, making normal cell regeneration difficult, and due to factors released from the damaged tissue, inflammatory cells gather, and various cytokine, proteinases, and so on secreted therefrom cause collagen re-alignment of corneal parenchyma, and due to fibrosis formed in the wound treatment procedure, corneal loses its transparency, and together with new vessels, various materials leaked from vessels deposit in corneal, thereby causing corneal opacity.

The invention claimed is:

1. A method of treating intraocular pressure causing glaucoma in a patient, comprising:
providing an ophthalmic agent comprising angiogenin or a fragment thereof as an active ingredient and additionally, an ophthalmically acceptable carrier, wherein the fragment of angiogenin is a polypeptide having the amino acid sequence set forth in SEQ ID NO: 1; and
administering the ophthalmic agent to the patient, wherein the ophthalmic agent comprising angiogenin or a fragment thereof activates aqueous humor outflow due to NO generation increase, Schlemm's canal expanding, and intercellular intervals widening, thereby reducing intraocular pressure, wherein the intraocular pressure causing glaucoma is treated by reducing intraocular pressure.

2. The method of claim 1, the ophthalmic agent further comprising:
at least one additive selected from the group consisting of a surfactant, an adjuvant containing an additional medicament, a buffer, an anti-oxidant, a stress adjuster, a preservative, a thickener, and a viscosity reformer.

* * * * *